(12) United States Patent
Hettwer

(10) Patent No.: US 12,201,747 B2
(45) Date of Patent: Jan. 21, 2025

(54) COMPOSITIONS AND METHODS FOR TREATMENT OF BONE DEFECTS

(71) Applicant: HETTWER HOLDING APS, Copenhagen (DK)

(72) Inventor: Werner Herbert Hettwer, Copenhagen (DK)

(73) Assignee: EMBIOS GMBH, Munich (DE)

( * ) Notice: Subject to any disclaimer, the term of this patent is extended or adjusted under 35 U.S.C. 154(b) by 328 days.

(21) Appl. No.: 17/317,540

(22) Filed: May 11, 2021

(65) Prior Publication Data

US 2021/0402058 A1 Dec. 30, 2021

Related U.S. Application Data

(63) Continuation of application No. 15/765,759, filed as application No. PCT/DK2016/050320 on Oct. 4, 2016.

(30) Foreign Application Priority Data

Oct. 5, 2015 (DK) .......................... PA 2015 70626

(51) Int. Cl.
  *A61L 27/36* (2006.01)
  *A61L 27/02* (2006.01)
  *A61L 27/12* (2006.01)
  *A61L 27/54* (2006.01)

(52) U.S. Cl.
  CPC ........... *A61L 27/365* (2013.01); *A61L 27/025* (2013.01); *A61L 27/12* (2013.01); *A61L 27/3608* (2013.01); *A61L 27/54* (2013.01); *A61L 2300/404* (2013.01); *A61L 2300/406* (2013.01); *A61L 2430/02* (2013.01)

(58) Field of Classification Search
None
See application file for complete search history.

(56) References Cited

U.S. PATENT DOCUMENTS

| | | |
|---|---|---|
| 5,366,507 A | 11/1994 | Sottosanti |
| 8,702,809 B2 | 4/2014 | Nauman et al. |
| 9,180,137 B2 | 11/2015 | Sandell et al. |
| 9,579,421 B2 | 2/2017 | Bhat et al. |
| 2004/0157798 A1 | 8/2004 | Little |
| 2010/0137417 A1 | 6/2010 | Chappell et al. |
| 2015/0283291 A1 | 10/2015 | Vogt |
| 2016/0231056 A1 | 8/2016 | Wei et al. |

FOREIGN PATENT DOCUMENTS

| | | |
|---|---|---|
| CA | 2884982 A1 | 10/2015 |
| WO | WO-2014/128217 A1 | 8/2014 |
| WO | WO-2017/059863 A1 | 4/2017 |

OTHER PUBLICATIONS

Campoccia et al., "A review of the biomaterials technologies for infection-resistant surfaces," Biomaterials vol. 37, No. 34, pp. 8533-8554 (2013).
Rabin, N. et al., "Agents that inhibit bacterial biofilm formation," Future Medical Chemistry, vol. 7, No. 5, pp. 647-671 (2015).
European Patent Application No. 16788416.2, Communication Pursuant to Article 94(3) EPC, dated Aug. 30, 2019.
Ginebra et al., Calcium phosphate cements: Competitive drug carriers for the musculoskeletal system?, Biomaterials, 27(10):2171-7 (2006).
International Application No. PCT/DK2016/050320, Demand for Preliminary Examination, filed Aug. 7, 2017.
Notice of Opposition Against European Patent No. EP3359209, filed by Bone Support AB, filed Sep. 7, 2021.
Richelsoph et al., Elution behavior of Daptomycin-loaded calcium sulfate pellets: A preliminary study, Clinical, Orthopaedics and Related Research, No. 461, pp. 68-73 (2007).
Constantz, B., et al., "Skeletal Repair by in Situ Formation of the Mineral Phase of Bone," *Science*, 1995, vol. 267; pp. 1796-1799.
Sanchez-Sotelo, J., et al., "Treatment of fractures of the distal radius with a remodellable bone cement," *The Journal of Bone & Joint Surgery*, 2000, vol. 82-B(6), pp. 856-863.

*Primary Examiner* — David J Blanchard
*Assistant Examiner* — Daniel F Coughlin
(74) *Attorney, Agent, or Firm* — Womble Bond Dickinson (US) LLP

(57) ABSTRACT

The present invention relates to the field of treatment of bone defects. The invention provides a composition for treatment of bone defects as well as methods for treatment of such defects.

17 Claims, 11 Drawing Sheets

COMPOSITIONS AND METHODS FOR TREATMENT OF BONE DEFECTS

FIELD OF INVENTION

The present invention relates to the field of treatment of bone defects. The invention provides a composition for treatment of bone defects as well as methods for treatment of such defects.

BACKGROUND OF INVENTION

Bone defects represent a common orthopaedic problem and can be a significant challenge to treat. They can arise as a consequence of disturbances or failure of formation and/or differentiation (bone aplasias and dysplasias), trauma, destruction due to a pathological process (infection, inflammation, tumors and implant wear associated osteolysis) or a surgical intervention or any combination of these.

The three principal factors beneficial for the treatment of any bone defect regardless of its etiology, namely osteoconductive, osteoinductive and osteogenetic properties have been known for decades. In 2007, Giannudis et al added to these another vitally important factor, mechanical stability, coining the "diamond concept" of bone defect reconstruction.

However, a single best method for optimal delivery of these four properties in any given situation with its own special circumstances particular to the respective individual case does not exist and has yet to be described.

Every year, many patients with benign bone tumors of greatly diverse etiology are treated. In addition, there is an increasing need for reconstruction of bone destruction secondary to metastatic bone disease (MBD) in a growing number of patients.

An optimal method for surgical reconstruction of metastatic bone defects has yet to be described and in absence of better alternatives, such defects have traditionally been managed with either implantation of allograft bone or bone cement (poly-methyl-methacrylate, PMMA). However, the bone remodeling capacity of allograft bone is limited, as this is an essentially dead material containing only a rather small amount of osteoinductive factors and PMMA prevents any bone formation altogether.

Furthermore, recurrent disease, particularly in more aggressive tumor types is not uncommon and hence the use of numerous adjuvant treatments have been described. Systemic administration of bisphosphonates, in this context, is well known to strongly inhibit osteoclast mediated bone destruction in primary and secondary bone tumors.

SUMMARY OF INVENTION

Drawbacks of conventional bone graft substitutes include delayed or absent resorption, which may restrict or even block bone ingrowth and formation of new bone. In addition, some bone graft substitutes are associated with unpredictable in situ maintenance of their solid structure, which has led to treatment cases where adequate mechanical stability of the bone reconstruction construct was not sufficiently maintained and a stable osteoconductive scaffold was not achieved.

Accordingly there is a need for new and effective materials and methods for treatment of bone defects. Mechanical stability is necessary to allow an undisturbed biological healing process, physiological remodeling and regeneration of bone. In one embodiment the present invention provides a multi-phasic biodynamic scaffold useful for assembly and for building in situ to accommodate the individual characteristic of the individual bone defect.

The invention thus provides a kit-of-parts comprising a bone reconstruction composition comprising a biocompatible carrier and at least one bioactive agent and a biocompatible matrix comprising solids particles and/or scaffolds of natural or synthetic origin. The solid particles and/or scaffolds may contribute to mechanical stability.

In one aspect, the present disclosure also provides a composition comprising a bone reconstruction composition comprising a biocompatible carrier and at least one bioactive agent and a biocompatible matrix comprising solids particles and/or scaffolds of natural or synthetic origin.

The components of the kit-of-parts may be used in a layered application and subsequent impaction achieves a firmly interdigitated three dimensionally solid composite structure. After curing of the composite filling the interspaces, said structure optimally fits the individual defect geometry and has vastly improved mechanical properties making it substantially more resistant to bending and shears forces. Thus, typically after 6 weeks and even more after 3 to 6 month from surgery, bone re-growth and remodeling is observed and there is no sign of liquefaction of the composite, as can also be seen from the pictures in the drawings.

Thus, the invention provides methods for treatment of a bone defect in an individual in need thereof, which method comprises
  providing a bone reconstruction composition comprising a biocompatible carrier (e.g. hydroxyapatite) and at least one bioactive agent,
  providing a biocompatible matrix comprising solids particles and/or scaffolds of natural or synthetic origin
  contacting the site of the bone defect in said individual with alternating layers of said composition and biocompatible matrix thereby treating said bone defect.

The disclosure also provides a method for treatment of a bone defect in an individual in need thereof, which method comprises
  providing a bone reconstruction composition comprising hydroxyapatite, a calcium salt and an antiresorptive agent,
  providing a bone graft material comprising bone from a human or non-human animal
  contacting the site of bone defect in said individual with alternating layers of said composition and said bone graft material
thereby treating said bone defect.

The present disclosure also provides a method for bone reconstruction in an individual suffering from a bone defect, said method comprising performing the method according to any one of the preceding claims, thereby obtaining growth of healthy bone on the site of the bone defect in said individual.

The invention also provides kit-of-parts comprising
  a bone reconstruction composition comprising an osteoconductive carrier (e.g. hydroxyapatite) and at least one bioactive agent,
  a biocompatible matrix comprising solids particles and/or scaffolds of natural or synthetic origin.

The invention also provides kit-of-parts comprising
  a bone reconstruction composition comprising hydroxyapatite, a calcium salt (e.g. calcium sulphate) and an antiresorptive agent (e.g. a bisphosphonate),
  a bone graft material comprising bone from a human or non-human animal.

The invention also provides kits-of-parts for use in the treatment of a bone defect in an individual in need thereof, wherein said kit-of-parts comprises or consists of
- a bone reconstruction composition comprising a biocompatible carrier (e.g. hydroxyapatite) and at least one bioactive agent,
- a biocompatible matrix comprising solids particles of natural or synthetic origin.

The invention also provides kits-of-parts for use in the treatment of a bone defect in an individual in need thereof, wherein said kit-of-parts comprises or consists of
- a bone reconstruction composition comprising hydroxyapatite, a calcium salt and an antiresorptive agent,
- a bone graft material comprising bone from a human or non-human animal.

The invention furthermore provides bone reconstruction compositions comprising a biocompatible carrier (e.g. hydroxyapatite), an antiresorptive agent (e.g. a bisphosphonate), and fosfomycin.

DETAILED DESCRIPTION OF THE INVENTION

Definitions

Figure 1:
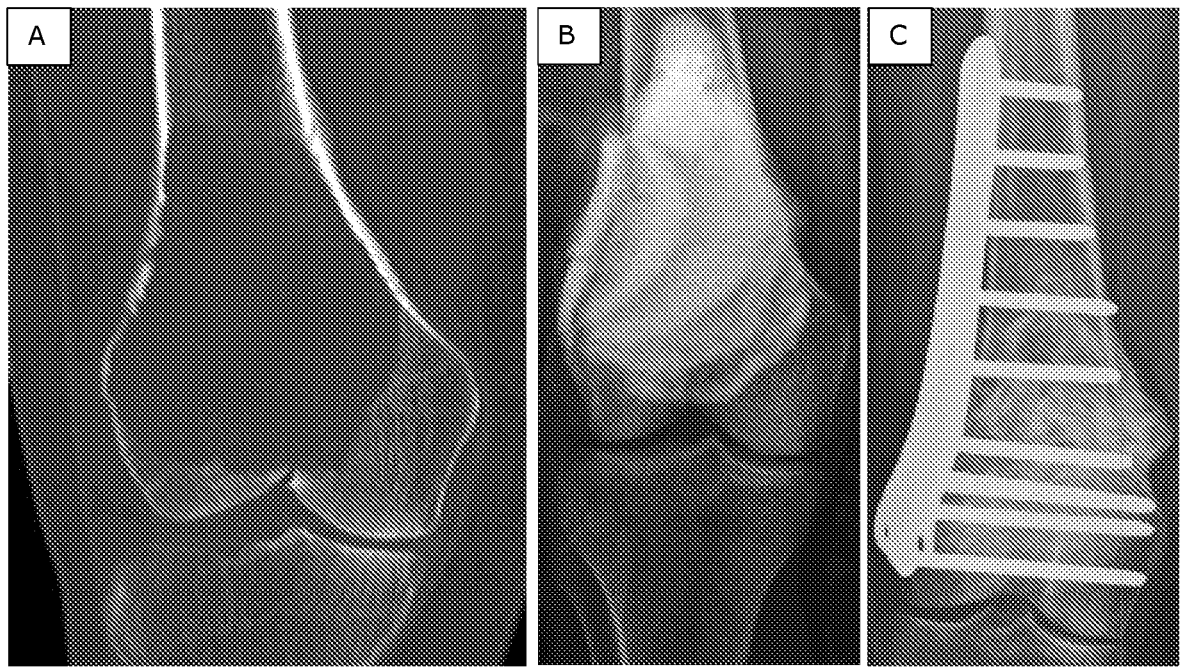
FIG. 1. 45 year old female with pathologic fracture through large giant cell tumor in the right distal femur, treated with open biopsy, curettage, burring, bone defect reconstruction with a combination of BGS/ZA and cancellous allograft, augmented with lateral locking plate osteosynthesis. Post-op x-rays and CT scans show progressive remodeling most prominent in the peripheral areas of the regenerate, as well as substantial periosteal bone formation (arrows). a. pre-operative; b. Post-operative and c. 6 months.
Figure 2:
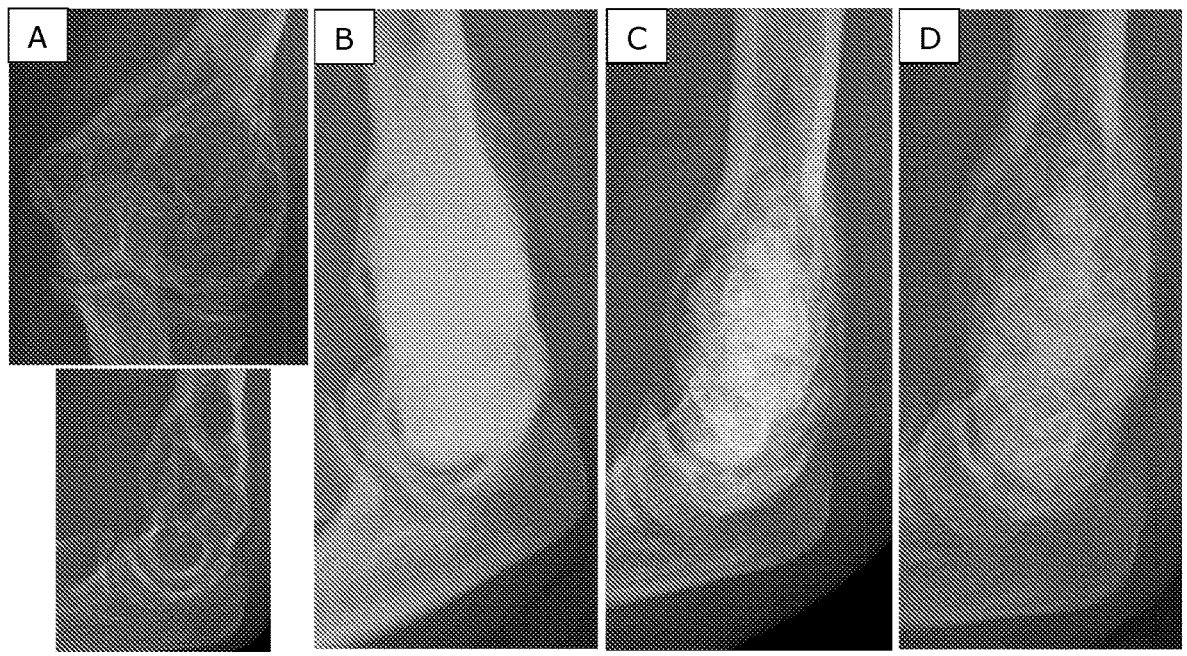
FIG. 2. 38 year old female with symptomatic vascular malformation with secondary aneurysmal bone in the left distal humerus, treated with open biopsy, curettage, burring, bone defect reconstruction with a combination of BGS/ZA and cancellous allograft. Post-op x-rays and CT scans show homogenous, progressive remodeling of the entire regenerate. a. pre-operative; b. post-operative; c. 3 months and d. 6 months.
Figure 3:
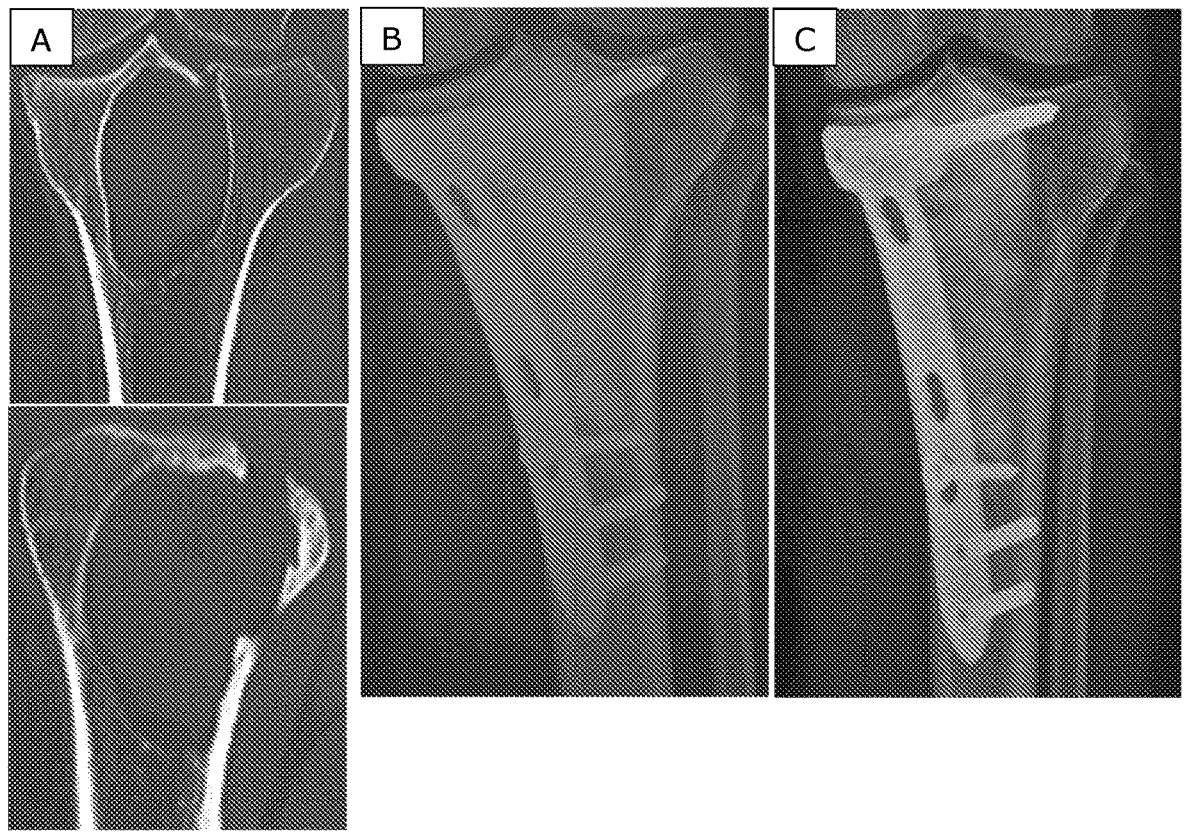
FIG. 3. 34 year old female with biopsy verified symptomatic PVNS in the left proximal tibia, treated, curettage, burring, bone defect reconstruction with a combination of BGS/ZA and cancellous allograft. Post-op x-rays show progressive remodeling of the entire regenerate. A. pre-operative; b. post-operative and c.6 months.
Figure 4:
FIG. 4. 26 year old female with symptomatic aneurysmal bone in the right femoral diaphysis verified by open biopsy and treated with curettage, burring, bone defect reconstruction with a combination of BGS/ZA and cancellous allograft and prophylactic fixation with a posterolateral locking plate. Post-op x-rays show progressive remodeling and no sign of local recurrence. A. pre-operative; b. post-operative and c.6 months.
Figure 5:
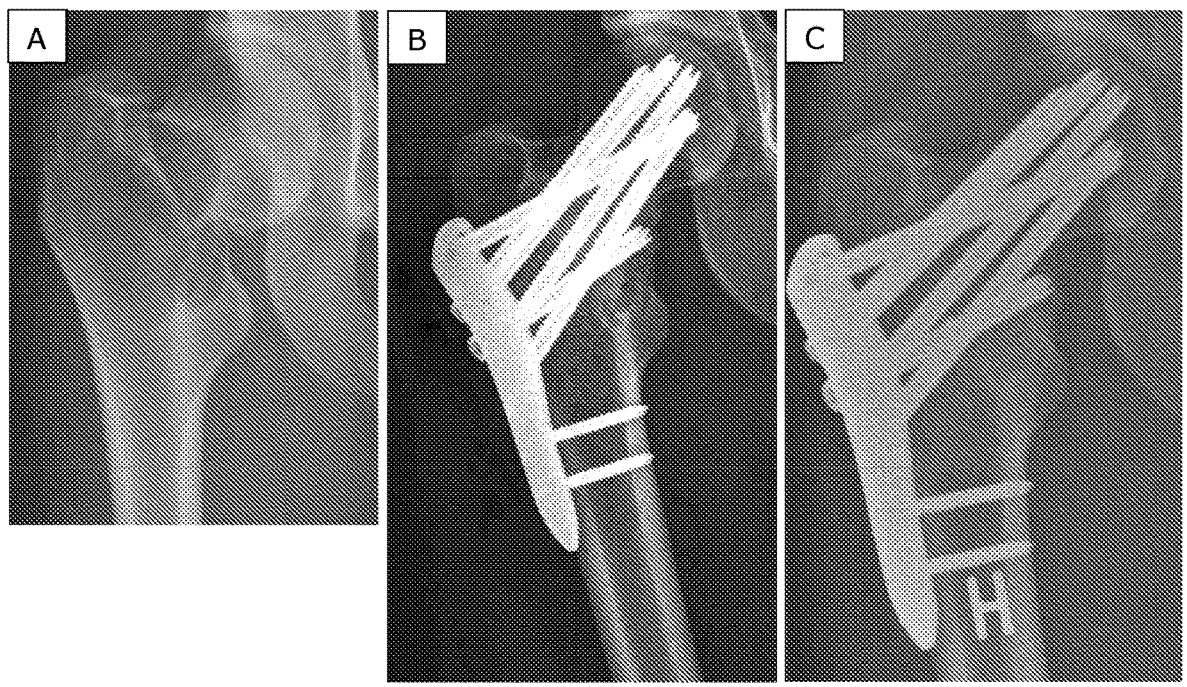
FIG. 5. 19 year old female with simple cyst and fracture in the right femur with minimal residual bone. The figures illustrate the reconstruction with locking plate and impaction grafting with allograft; BGS with zoledronic acid and demineralized bone matrix (DBM). 6 week x-ray shows healing. a. pre-operative; b. post-operative and c. 6 weeks.

The term "biocompatible matrix" as used herein refers to a composition comprising solid particles and/or scaffolds of natural or synthetic origin. Said biocompatible matrix is preferably mechanically stable, and thus may be capable of providing mechanical stability to bone. Said particles and/or scaffolds are biocompatible meaning that they can coexist with living tissues without causing harm. Preferably said particles may slowly be resorbed by osteoclasts and subsequently replaced by newly formed bone through osteoblastic activity, or alternatively, the particles may permanently osseointegrate. By "osseointegrate" it is understood that a direct structural and functional connection is formed between living bone and the surface of the particles and/or scaffolds, for example hydroxyapatite, allog raft bone or metal particles and/or scaffolds. The biocompatible matrix may be resorbable, slowly resorbable or non-resorbable. The biocompatible matrix may comprise or consist of a bone graft material. For example, the particles may comprise or consist of one or more selected from the group consisting of bone graft material (e.g. autograft and/or allograft bone graft material), synthetic metallic particles and/or scaffolds, synthetic non-metallic particles and/or scaffolds and any combination thereof.

The term "biocompatible carrier" as used herein refers to a composition comprising materials of natural or synthetic origin (e.g. calcium salts, polymers, collagen gels) which can coexist with living tissues without causing harm and are suitable vehicles for delivery of any bioactive agent to a living tissue, for example to the site of a bone defect. In some embodiments, the biocompatible carrier is an osteoconductive carrier. In some embodiments, the biocompatible carrier comprises an osteoconductive material. The term "osteoconductive" as used herein refers to a material that can serve as a scaffold for new bone growth that is perpetuated by the native bone. Osteoblasts from the margin of the defect that is being treated can utilize the osteoconductive material as a framework upon which to spread and generate new bone. An "osteoconductive material" is usually a material that can be in powder form, but can become a paste when mixed with a solvent. The so-formed paste can subsequently cure at physiological conditions e.g. in the site of a bone defect.

The term "bone" as used herein refers to natural bone from any animal. Bones typically comprise cortical bone and cancellous bone. Bone may also comprise other types of tissue, which may be referred to collectively as "soft tissue". The soft tissues include marrow, endosteum, periosteum, nerves, blood vessels and cartilage.

The term "bone graft material" as used herein refers to a material comprising bone from a human or non-human animal. Preferably, bone graft material consists exclusively of material from bone from a human or non-human animal. Bone graft material is preferably divided in particles.

The term "cancellous bone", also known as trabecular bone or spongy bone, as used herein refers to the bone composed of tiny lattice-shaped units, typically located internal to the hard compact bone at the metaphyeal ends of the long bones.

The term "cure" as used herein in relation to the bone reconstruction composition, refers to hardening of the composition. After mixing all ingredients of the bone reconstruction composition, the composition starts curing. The composition is considered "cured" if digital compression does not leave an impression.

The term "digital compression" as used herein refers to pushing hard with a finger.

The term "paste" as used herein refers to a composition of a sufficient high viscosity to allow physical application to a defined space without losing its shape. A composition is considered a "paste", when the interphase between the paste and surrounding air is not deformed when a container comprising the paste is being moved.

The term "individual" as used herein refers to a human or non-human animal.

The term "resorbable" as used herein refers to a material that can be targeted by osteoclasts, dissolved, and subsequently replaced by newly formed bone through osteoblastic activity. Resorbable materials can be polymers, ceramics, or composites. Examples of resorbable materials are calcium sulfate, calcium phosphate, hydroxyapatite, polymers, e.g. polylactcic acid, collagen foams or gels.

The term "treatment" as used herein may refer to any kind of treatment. The treatment may be a curative treatment, or it may also be an ameliorating treatment and/or a treatment reducing the effects of the bone defect. The treatment may also be a treatment which delays progression of a bone defect, for example the treatment may reduce the growth of metastatic bone disease.

Bone Reconstruction Compositions and Kit-of-Parts Comprising Same

The present invention relates to kits-of-parts for bone reconstruction, wherein said kits typically comprise a bone reconstruction composition and a biocompatible matrix. In particular, the biocompatible matrix may comprise or consist of a bone graft material. Examples of useful biocompatible matrices are described below. The bone reconstruction composition may comprise a biocompatible carrier and at least one bioactive agent. In particular, the bone reconstruction composition may comprise an osteoconductive material. Examples of useful biocompatible carriers and bioactive agents are provided below. In particular the osteoconductive material comprises or consists of hydroxyapatite and calcium salts. In particular, the at least one bioactive agent may be an antiresoprtive agent, such as a bisphosphonate. Said bone reconstruction composition may also comprise two or more bioactive agents that can add further beneficial effects for bone reconstruction. Examples of such bioactive agents are anti-microbial agents, antiresorptive agents, anti-tumor agents, bone growth-promoting osteoinductive and/or osteogenetic agents, and more as described in the section below "Bioactive agents". Said bone reconstruction composition may also comprise a solvent. In some embodiments, the bone reconstruction composition comprises a bioactive agent which is in liquid form and can act as a solvent.

The invention also provides a bone reconstruction composition per se, which comprises a biocompatible carrier, an antiresorptive agent such as bisphosphonate, and typically also an anti-microbial agent such as fosfomycin and/or other bioactive agents. Examples of useful biocompatible carriers, bisphosphonates, anti-microbial agents and other bioactive agents are provided below.

The bone reconstruction composition and the kit-of-parts are preferably prepared in such a way that they can be used to repair bone defects in vivo and stimulate bone growth in a subject affected by a bone defect. In particular, it is highly preferably that the bone reconstruction composition achieves a viscosity, which is sufficiently high so that it does not flow away from the site of the bone defect when added to said site. On the other hand, the bone reconstruction material should preferably be moldable for a sufficient amount of time to allow for optimal adaptation to the individual site and geometry during repair of the bone defect. Accordingly, it is preferred that the bone reconstruction composition may reach a beneficial degree of hardness within 2 to 60 minutes from mixing. In particular it is preferred that the bone reconstruction composition cures in a time range of 2 to 120 min, such as in the range of 2 to 60 minutes, for example in the range of 30 to 60 min. after all ingredients of said composition are mixed.

It is also preferred that the bone reconstruction composition hardens to a paste in a time range of 2 to 10 minutes, such as in a time range of 2 to 5 minutes, such as in a time range of 2 to 3 minutes after all ingredients of said composition are mixed.

It is also preferred that the bone reconstruction composition thickens to a paste in a time range of 2 to 10 minutes, such as in a time range of 2 to 5 minutes, such as in a time range of 2 to 3 minutes after all ingredients of said composition are mixed.

The bone reconstruction compositions may also comprise bioactive agents and therapeutic agents such as anti-microbial agents and/or antiresorptive agents, anti-tumor agents and growth-promoting agents that facilitate, enhance or protect the bone reconstruction. These bioactive agents and therapeutic agents may be released from the composition to the tissues around it in vivo in the treated individual. Examples of said bioactive agents are provided below.

In one embodiment, at least one bioactive agent is an antibiotic, as described in the section "Antibiotic". In another embodiment at least one bioactive agent is an antiresorptive agent. For example, the antiresorptive agent may be one of the bisphosphonates described in the section "Bisphosphonate". In a further embodiment, the bone reconstruction composition may comprise a growth promoting agent, which may be any of the bioactive agents described in the section "Growth promoting agent". Thus, the bone reconstruction composition may comprise any of the bioactive agents described herein below in the sections "Bioactive agent", "Bisphosphonate", "Antimicrobial agents", "Growth promoting agents" and "Other bioactive agents". In particular, the bone reconstruction composition may comprise both an antibiotic and an antiresorptive agent. Alternatively, the bone reconstruction may comprise only one of an antibiotic or an antiresorptive agent. In addition, the bone reconstruction composition may also comprise one or more additional bioactive agents.

The main components comprised in the bone reconstruction composition may have any of the features described in the following sections "Biocompatible carrier", "Bioactive agent", "Hydroxyapatite", "Bisphosphonate", "Calcium salt", "Antibiotic", and "Growth factor".

The kit-of-parts according to the invention typically comprises the bone reconstruction composition and a biocompatible matrix. The biocompatible matrix comprises solid particles of natural or synthetic origin. Said particles may be metallic or non-metallic synthetic particles or bone graft material, such as bone from a human or a non-human animal, and may be any of the materials described herein below in the section "Biocompatible matrix". Typically, the parts of the kit may be provided and stored separately.

Said kit-of-parts may be prepared for contacting the site of a bone defect in an individual in need thereof with alternating layers of bone reconstruction composition and biocompatible matrix such as a bone graft material in order to achieve the important mechanical stability of the resulting bone reconstruction construct to provide a mechanically undisturbed environment conductive to bone graft incorporation, remodeling and overall healing. Examples of useful methods for contacting the site of a bone defect are described herein below in the section "Treatment of bone defect". Said biocompatible matrix may be any of the materials described in the section below "Biocompatible matrix".

The bone reconstruction composition may be replaced by the healthy growing bone of the subject, said bone growing because of the beneficial effects of the compositions and methods described in the present invention.

Examples of effects obtained when applying said kit-of-parts for bone reconstruction in an individual in need are described in the section below "Treatment of bone defect".

Treatment of Bone Defects

The present invention describes methods for treatment of a bone defect in a subject, said treatment comprising providing a composition that promotes bone reconstruction, providing a biocompatible matrix e.g. a bone graft material, and providing impacting a bone defect with said composition and said biocompatible matrix in alternate layers. The composition may comprise different components as described in the section "Compositions for bone reconstruction".

In a preferred embodiment of the present disclosure, a bone defect is treated using the method as disclosed herein and described in detail in the section below "Method for bone reconstruction".

In a preferred embodiment of the present invention, the treatment comprises local administration of a composition and a bone graft material to a subject affected by a bone defect thereby allowing growth of healthy bone in place of a bone defect.

In one embodiment the method involves contacting the site of bone defect with alternating layers of said bone reconstruction composition and said biocompatible matrix e.g. a bone graft material. This in-situ additive layering may start with contacting the entire bone walls of the site of bone defect with the bone reconstruction composition. This may ensure that the biologically most active substances are delivered as close as possible to the target zone of initial remodeling and potential residual pathology. Said bone reconstruction composition is typically delivered in the form of a paste. After addition of said bone reconstruction composition the biocompatible matrix may be added.

In some embodiments of the present disclosure, the bone reconstruction composition and the biocompatible matrix e.g. a bone graft material are applied to the bone defect by injection and/or moulding.

Thus, the method may comprise the steps of:
a) contacting the bone walls of the site of the bone defect to be treated with the bone reconstruction composition of the invention, wherein the bone reconstruction composition preferably is in the form of a paste; and
b) contacting the bone reconstruction composition with a layer of said biocompatible matrix;
c) contacting the biocompatible matrix with a layer of said bone reconstruction composition;
d) optionally repeating steps b) and c) 1 to 20 times, such as 1 to 10 times, for example 1 to 5 times, such as 1 to 3 times depending on the size of the bone defect, so that or few layers are used to fill a small bone defect, whereas several layers are used to fill a large bone defect.

Before step a) the method may comprise contacting the site of the bone defect with one or more active compounds, e.g. with an antiresorptive agent, such as a bisphosphonate, with an antimicrobial agent such as an antibiotic and/or with a growth promoting agent, such as a BMP.

In some embodiments of the present disclosure, Zoledronic acid or a pharmaceutically acceptable salt thereof is administered locally to the site of the bone defect prior to performing step a).

In one embodiment of the present invention, bone density measurements with dual energy x/ray absorptiometry (DEXA) are performed before and after treatment to assess the state of the bone. In a preferred embodiment, the values do not change significantly in the time following treatment with the kit-of-parts and methods according to the present invention. Exemplary values before treatment are at least 1.5 g/cm$^2$ and not higher than 3 g/cm$^2$. In an individual treated with traditional methods, said values would typically drop to at least 0.1 g/cm$^2$ and not higher than 1 g/cm$^2$ after treatment. In an individual treated with the kit-of-parts and methods according to the present invention, said values would remain constant and thus be at least 1.5 g/cm$^2$ and not higher than 3 g/cm$^2$ after at least 6 weeks, such as at least 12 weeks after treatment, indicating that bone has replaced the composition.

The methods for treatment of a bone defect in a subject disclosed herein may be supplemented by the use of appropriate internal or external bone fixation devices to establish or protect mechanical integrity of the entire bone in which the defect is treated. As these foreign bodies represent a risk for microbial colonization and biofilm formation, therapeutic- and/or preventive antimicrobial biofilm agent application to the surface of the implant may be needed. The bioactive agents described in the sections "Bioactive agents", "Antibiotics" and "Other bioactive agents" can be used for this purpose. Said agents may be applied as preliminary surface treatment (e.g. surface coating with antimicrobial agents such as silver, copper, antibiotics or others). Said agents may also be used for in-situ surface modification of the surface of the implant e.g. with antibiotic- and/or antibiofilm agents.

In some embodiments of the present disclosure, the biocompatible carrier comprises at least one bioactive agent, wherein said bioactive agent prevents and/or treats microbial colonization and biofilm formation of the particles of the biocompatible matrix.

In some embodiments of the present disclosure, the biocompatible carrier comprises at least one bioactive agent, wherein said bioactive agent prevents and/or treats microbial colonization and biofilm formation of any internal or external bone fixation device used for treating a bone defect.

Bone Defect

The present invention describes methods, kits-of-parts and bone reconstruction compositions that are useful for treatment of a variety of bone defects in a subject. For example said individual may be an individual suffering from cancerous bone diseases, for example metastatic bone lesions; primary bone cancer, for example osteosarcoma; benign bone tumors, for example giant cell tumor of bone; inflammation or infection of the bones; and one or more bone fractures, for example pathologic fractures, and thus, said bone defect may be any of the aforementioned or caused by any of the aforementioned conditions.

The bone reconstruction compositions, the kits-of-parts as well as the methods can also be used to reconstruct a gap, a bone void, or a pre-existing bone cavity. Accordingly, the bone defect may be a partial or complete structural gap, a so-called segmental bone defect, or a bone void or a pre-existing bone cavity, so-called cavitary bone defect.

The bone reconstruction compositions, the kits-of-parts as well as the methods can be used in a wide variety of applications, such as in the treatment of bone defects associated with trauma and fracture healing, prosthetic implants, and implants of foreign materials in other situations and bone loss due to congenital, infective or iatrogenic causes. Such situations may comprise filling a gap or a bone void or a pre-existing bone cavity, such as fractures, osteotomy, for the attachment of prostheses or other foreign material, for prosthetic revision surgery, for plastic surgery, for reconstruction surgery, or for cosmetic surgery.

The bone reconstruction compositions, the kits-of-parts as well as the methods are suitable for local use in tooth pockets and/or bifurcatures to treat periodontitis or to be combined with other treatment options for periodontitis included therein, such as supportive matrix proteins or locally acting growth inducing factors.

Likewise, they can be used together with collagen membranes or other supports, which are of importance for the growth of supportive tissues.

The bone reconstruction compositions, the kits-of-parts as well as the methods can be used for repairing osteochondral defects as well as fractures or bone defects involving a joint.

The bone reconstruction compositions, the kits-of-parts as well as the methods can be used to fill skeletal defects caused by the removal of orthopedic devices, which are utilized for internal or external fixation of fractures, for example screws and pin tracts. It is in such occasions preferred that antibiotics are included in the composition as additives. They can also be used for filling of a bone cavity or replacing bone lost during surgical removal of a tumor.

The bone reconstruction compositions, the kits-of-parts as well as the methods can be used for local treatment of infections or infestations in the musculoskeletal system, such as osteomyelitis caused by e.g. bacteria or fungi. A combined osteoplastic and local antimicrobial treatment and a prophylaxis of skeletal infection can thus be obtained, e.g. in sternotomies, prosthetic implants, reconstructive surgery, trauma surgery, cancer surgery, cosmetic surgery, and oromaxillo-facial surgery.

The bone reconstruction compositions, the kits-of-parts as well as the methods can also be used for local treatment with cytostatic or anti-tumor agents, such as in musculoskeletal tumors, e. g. for treatment of metastases in bone, e.g. in vertebrae. The metastases may be from any primary cancer, such as breast or prostatic cancers. The primary cancer may be a cancer demanding treatment with a supportive material that concomitantly gives a possibility for local treatment with anti-tumor agents. Furthermore, it can be used locally together with agents that enhance the clinical effects of irradiation in diseases, such as tumor diseases. A list of relevant anti-tumor agents that can be incorporated in the bone reconstruction composition as bioactive agents can be found on https://www.cancer.gov/about-cancer/treatment/drugs.

In one embodiment the bone defect is caused by an inflammation and/or by an infection of the bone.

In one preferred embodiment of the invention the bone defect is a bone tumor, such as giant cell tumor of bone and/or the bone defect is associated with or caused by a bone tumor, such as giant cell tumor of bone.

In another preferred embodiment of the invention the bone defect is metastatic bone disease. Many primary tumors metastasize to other locations in the body, for example bone. Cancer which has metastasized to bone may be referred to as "metastatic bone disease". A metastasis to the bone may cause bone cavities. For example, metastases may be removed from the bone by surgery leaving a bone cavity. Bone cavities caused by or associated with metastases to the bone may be filled using the bone reconstruction compositions, the kits-of-parts and/or the methods of the present invention.

Biocompatible Carrier

The bone reconstruction compositions described by the present disclosure comprise a biocompatible carrier.

Said biocompatible carrier may be a controlled releasing polymer matrix, for example comprising a synthetic polymer, such a synthetic polymer with pendant-functionalized diols, polyethylene glycol, polyacrylic acid, polyesters and their co-plymers e.g. polycaprolactone, polyanhydrides e.g. polyanhydrides based on sebacic acid (SA), p-(carboxyphenoxy)propane (CPP), p-(carboxyphenoxy)hexane (CHP) and their copolymers, polyamides, polyorthoesters (POE), e.g. POE I, POE II, POE III and POE IV; recombinant proteins-based polymers, in-situ forming hydrogels (such as PHEMA, and copolymers of PVA or PEG with acrylamides).

Said biocompatible carrier may be a controlled releasing polymer matrix, for example comprising a natural polymer e.g. proteins such as collagen, gelatin and fibrin; polysaccharides such as hyaluronic acid and alginate; cellulose derivatives, chitosan, polysaccharide-based polymers and natural protein-based polymers.

Said biocompatible carrier comprising a releasing polymer matrix may comprise polymers as described above in pure form or as part of drug delivery systems such as nanoparticles and microparticles, dendrimers, nano- and micro-spheres, capsosomes and micelles.

In some embodiments, the biocompatible carrier comprised in the bone reconstruction composition comprises an osteoconductive resorbable material.

The biocompatible carrier is typically used as a carrier for one or more bioactive agents. The bioactive agents may further enhance the growth of the natural bone and/or have a therapeutic effect for treatment of the bone defect or a disease associated therewith. In some embodiments, the biocompatible carrier comprises an osteoconductive material and so it favors growth of natural bone via the action of osteoblasts and osteoclasts. In other embodiments, the biocompatible carrier does not comprise an osteoconductive material.

In preferred embodiments of the present disclosure, the biocompatible carrier comprises calcium salts and/or hydroxyapatite, as described below. In further embodiments of the present disclosure, the biocompatible carrier comprises hydroxyapatite and polymers. It is preferred that the biocompatible carrier comprises both calcium salt(s) and hydroxyapatite, which may be any of the calcium salts and hydroxyapatites described below.

Calcium Salt

The biocompatible carrier of the present disclosure may comprise calcium salts. Said calcium salt may be any useful calcium salt. For example the calcium salt may be selected from the group consisting of calcium sulfate and calcium phosphate.

In some embodiments of the invention the biocompatible carrier comprises more than one calcium salt, and thus the calcium salt may be a mixture of at least two different calcium salts. Thus, the calcium salt may for example comprise at least one calcium phosphate component and at least one calcium sulfate component.

In other embodiments the calcium salt comprises only one calcium salt.

Calcium sulfate may particularly be hardened calcium sulfate, such as hardened calcium sulfate that has a diameter which is less than 100 μm.

In one embodiment of the present invention, calcium sulfate represent up to 100% of the calcium salts. In another embodiment, the particulate hardened calcium sulfate is calcium sulfate dihydrate (gypsum).

In one embodiment of the present disclosure, the biocompatible carrier does not comprise calcium sulfate.

Hydroxyapatite

The biocompatible carrier of the present disclosure may comprise the calcium-rich mineral hydroxyapatite (HA). HA is a naturally occurring mineral and has the general formula $Ca_5(PO_4)_3(OH)$, usually written $Ca_{10}(PO_4)_6(OH)_2$ because its crystal unit is a dimer. Up to 50% by volume and 7% by weight of human bone is a modified form of HA and HA is also known as bone mineral.

When preparing the bone reconstruction composition, then typically the HA is mixed with the calcium salt. The ratio between the calcium salt and HA is typically in the following ranges:

30 to 50 parts HA: 50 to 70 parts calcium salt, e.g. calcium sulfate, calcium phosphate or other salts 35 to 45 parts HA: 55 to 65 parts calcium salt, e.g. calcium sulfate, calcium phosphate or other salts 40 parts HA: 60 parts calcium salt, e.g. calcium sulfate, calcium phosphate or other salts.

The bone reconstruction composition may comprise at least 40% of said mixture of HA and calcium salt, for example at least 50% of said mixture of HA and calcium salt, such as in the range of 40 to 70%, for example in the range of 50 to 70%, such as in the range of 50 to 60% of said mixture of HA and calcium salt.

Bioactive Agents

The bone reconstruction compositions described by the present disclosure comprise at least one bioactive agent. The at least one bioactive agent is usually comprised in the biocompatible carrier.

In some embodiments of the present disclosure, a bioactive agent is applied directly to the solid components of the biocompatible matrix, for example silver or hydroxyapatite can be used to coat trabecular titanium spheres, or antibiotics, anti-biofilm and antiresorptive agents can be adsorbed onto purified allograft bone.

In some embodiments of the present disclosure the biocompatible carrier comprises one or more bioactive agents selected from the group consisting of antiresorptive agents, antibiotics, antibacterial agents, anti-biofilm agents, antiadhesive agents, antibodies, growth and differentiation factors, cytokines, bone morphogenetic proteins (BMP) antagonist inhibitors, signaling proteins, human cell suspensions, solvents, anti-tumor agents and radioactive material or combinations thereof.

The bone reconstruction composition of the present disclosure comprises, in some embodiments, two or more bioactive agents, wherein any one of the two or more bioactive agent is any one of the bioactive agents described herein.

In some embodiments of the present disclosure, the bone reconstruction composition is in the form of a paste and comprises two or more bioactive agents, wherein at least one of the bioactive agents accelerates curing of the paste and wherein at least one of the bioactive agents decelerates curing of the paste.

Most additives and bioactive agents have a decelerating effect curing of the paste of the composition and a destabilizing effect on the mechanical properties of the biocompatible carrier in-situ. Therefore, in some embodiments an agent that accelerates curing of the composition may be added. Said agent that accelerates curing of the bone reconstruction composition and improves its stability may be added by titration.

In a preferred embodiment of the present disclosure, the bioactive agent that accelerates curing of the composition is an antibiotic, for example fosfomycin or a pharmaceutically acceptable salt thereof.

In a preferred embodiment of the present disclosure, the bioactive agent that accelerates curing of the composition is fosfomycin or a pharmaceutically acceptable salt thereof and said fosfomycin or a pharmaceutically acceptable salt thereof is dissolved in a solvent.

In a further preferred embodiment of the present disclosure, the bioactive agent that decelerates curing of the composition is a bisphosphonate, for example a bisphosphopnate selected from a group consisting of Zoledronic acid, Pamidronic acid, Neridronic acid, Olpadronic acid, Alendronic acid, Ibandronic acid, Risedronic acid, pharmaceutically acceptable salts of any of the aforementioned and combinations of any of the aforementioned. For example, the bone reconstruction composition may comprise a bisphosphonate in an amount comprised between 0.08 and 0.2 g/ml, so 10 ml of compositions may comprise between 0.8 and 2 g of bisphosphonate.

Bisphosphonate

In some embodiments of the present disclosure, the bone reconstruction compositions comprise a bisphosphonate. The term "bisphosphonate" as used herein refers to a class of medicaments that prevent the loss of bone mass. This class of medicaments is also referred to as antiresorptive agents, as they slow or block the resorption of bone.

In a preferred embodiment of the present invention, the antiresorptive agent used is a bisphosphonate. In a further embodiment, the antiresorptive agent is a compound having antiresorptive activity but not the structure of a bisphosphonate, for example a monoclonal antibody such as Denosumab.

Preferably bisphosphonates to be used with the present invention have the general structure of formula (I):

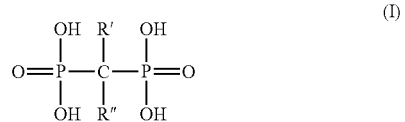

The bisphosphonates to be used with the present invention are preferably compounds of formula (I), which are specific inhibitors of osteoclasts. By inhibiting osteoclasts, the bisphosphonates inhibit bone loss.

Typically, R' may be a small moiety, for example R' may be selected from the group consisting of —H, —OH and halogen. In a preferred embodiment R' is —OH, which enhances binding to hydroxyapatite.

R" may be a larger moiety although it is also comprised in the invention that R" may be a small moiety such as halogen or methyl. Preferably, however R" is —$C_{1-6}$-alkyl-X, wherein X is selected from the group consisting of cyclic, aryl, heteroaryl and amine. In particular, X may be amine or a mono- or bicyclic heteroaryl, wherein at least one heteroatom of said heteroaryl is nitrogen. Said amine may be a primary amine, for example —$NH_2$, a secondary amine or a tertiary amine. Said tertiary amine may be —$N(R_1)(R_2)$, wherein $R_1$ and $R_2$ independently are $C_{1-6}$-alkyl. Said mono- or bicyclic heteroaryl, wherein at least one heteroatom of said heteroaryl is nitrogen may for example be imidazole, pyridine or pyrrolidine.

In one embodiment of the invention the bisphosphonate is a nitrogen containing bisphosphonate. Thus, the bisphosphonate may be a bisphosphonate of formula (I), wherein at least one of R' and R" contains nitrogen.

In one embodiment the bisphosphonate is selected from the group consisting of Zoledronic acid, Pamidronic acid, Neridronic acid, Olpadronic acid, Alendronic acid, Ibandronic acid, Risedronic acid and pharmaceutically acceptable salts thereof. The bone reconstruction compositions may also comprise more than one bisphosphonate, for example the bone reconstruction compositions may comprise a combination of two or more of the aforementioned bisphosphonates.

In another embodiment the bisphosphonate is a nitrogen containing bisphosphonate, for example selected from the group consisting of Zoledronic acid, Alendronic acid, Risedronic acid and pharmaceutically acceptable salts thereof.

In a preferred embodiment of the invention, the bisphosphonate is Zoledronic acid (ZA) or a pharmaceutically acceptable salt thereof. In particular the bisphosphonate may be Zoledronic acid. Zoledronic acid may also be referred to as zoledronate. Zoledronic acid is a compound of the formula (II):

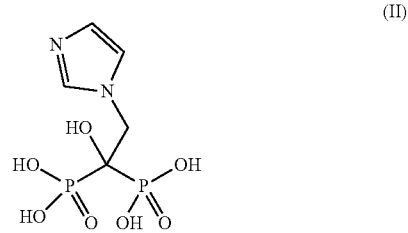 [SMILES: O=P(O)(O)C(O)(Cn1ccnc1)P(=O)(O)O]

Zoledronate has multiple anti-tumor effects, including direct induction of cell death in various types of tumor, such as lung-, breast, prostate and kidney cancer, myeloma and giant cell tumor of bone.

The bisphosphonate may be present within the composition in any suitable amount. For example, the bone reconstruction composition may comprise in the range of 0.1 to 1.5 mg/ml, such as in the range of 0.2 to 1 mg/ml, for example in the range of 0.2 to 0.0 mg/ml, such as in the range of 0.3 to 0.8 mg/ml of said bisphosphonate. In one embodiment the bone reconstruction composition comprises approximately 0.3 mg/ml of bisphosphonate. In one embodiment the bone reconstruction composition comprises approximately 0.55 mg/ml. In one embodiment the bone reconstruction composition comprises approximately 0.80 mg/ml. ml refers to the final volume of the bone reconstruction composition and the term "approximately" as used herein refers to +/−10%, such as +/−5%, for example +/−1%.

In a preferred embodiment of the present disclosure, 10 ml of bone reconstructing composition comprises between 1 and 2.5 ml of said Zoledronic acid or pharmaceutically acceptable salt thereof, such as between 1 and 1.5 ml, such as between 1 and 2 ml, such as between 1.5 and 2 ml, such as between 1.5 and 2.5 ml, such as between 2 and 2.5 ml f said Zoledronic acid or pharmaceutically acceptable salt thereof.

In a preferred embodiment of the present disclosure, 10 ml of bone reconstructing composition comprises between 0.2 and 2 g of said Zoledronic acid or pharmaceutically acceptable salt thereof, such as between 0.2 and 1.5 g, such as between 0.2 and 1 g, such as between 0.2 and 0.5 g, such as between 0.5 and 2 g, such as between 0.5 and 1.5 g of said Zoledronic acid or pharmaceutically acceptable salt thereof.

Antimicrobial Agents

The compositions described by the present invention may comprise anti-microbial agents, such as antibiotics. Said agents may be released from the composition in vivo and therefore prevent, limit or treat infection in the treated subject.

Such compounds include natural antibiotics as well as other semisynthetic and synthetic antibacterial or bacteriostatic compounds, which are acting against pathogenic and/or infectious microorganisms, e.g. staphylococci. Non-limiting examples of antibiotics which can be used with the invention includes fosfomycin, gentamicin, tetracycline-HCl, vancomycin, Amikacin, Gentamicin, Kanamycin, Neomycin, Netilmicin, Tobramycin, Paromomycin, Streptomycin, Spectinomycin, Geldanamycin, Herbimycin, Rifaximin, Loracarbef, Ertapenem, Doripenem, Imipenem/Cilastatin, Meropenem, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefotaxime, Cefpodoxime, Ceftazidime, Ceftibuten, Ceftizoxime, Ceftriaxone, Cephalosporins (Fourth generation), Cefepime, Maxipime, Cephalosporins (Fifth generation), Ceftaroline fosamil, Ceftobiprole, Clycopeptides, Teicoplanin, Telavancin, Dalbavancin, Oritavancin, Lincosamides, Clindamycin, Lincomycin, Lipopeptide, Daptomycin, Macrolides, Azithromycin, Clarithromycin, Dirithromycin, Erythromycin, Roxithromycin, Troleandomycin, Telithromycin, Spiramycin, Monobactams, Aztreonam, Nitrofurans, Furazolidone, Nitrofurantoin, xazolidinones(Bs), Linezolid, Posizolid, Radezolid, Torezolid, Penicillins, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Amoxicillin/clavulanate, Ampicillin/sulbactam, Piperacillin/tazobactam, Ticarcillin/clavulanate, Polypeptides, Bacitracin, Colistin, Polymyxin B, Quinolones/Fluoroquinolone, Ciprofloxacin, Enoxacin, Gatifloxacin, Gemifloxacin, Levofloxacin, Lomefloxacin, Moxifloxacin, Nalidixic acid, Norfloxacin, Ofloxacin, Sulfonamides (Bs), Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), Sulfonamidochrysoidine (archaic), Tetracyclines(Bs), Demeclocycline, Doxycycline, Minocycline, Oxytetracycline, Tetracycline, Clofazimine, Dapsone, Capreomycin, Cycloserine, Ethambutol (Bs), Ethionamide, Isoniazid, Pyrazinamide, Rifampicin (Rifampin in US), Rifabutin, Rifapentine, Streptomycin, Arsphenamine, Chloramphenicol(Bs), Fosfomycin, Fusidic acid, Metronidazole, Mupirocin, Platensimycin, Quinupristin/Dalfopristin, Thiamphenicol, Tigecycline(Bs), Tinidazole, or Trimethoprim(Bs).

In a preferred embodiment of the present disclosure, the antibiotic is selected from the group consisting of fosfomycin, gentamicin, tetracycline, vancomycin, tobramycin, gentamycin, cephalosporin and a combination thereof.

In a preferred embodiment of the present disclosure, the at least one bioactive agent comprises or consists of fosfomycin or a pharmaceutically acceptable salt thereof.

For example, the bone reconstruction composition comprises at least 80 mg/ml of fosfomycin, such as at least 97 mg/ml, such as at least 110 mg/ml, and up to 200 mg/ml, such as up to 175 mg/ml of fosfomycin or pharmaceutically acceptable salt thereof, where ml refers to the final volume of the composition.

In a preferred embodiment of the present disclosure, the biocompatible carrier comprises an osteoconductive material such as hydroxyapatite and at least one bioactive agent, such as fosfomycin or a pharmaceutically acceptable salt thereof.

In a further embodiment of the present disclosure, the biocompatible carrier comprises an osteoconductive material such as hydroxyapatite and a bisphosphonate, such as Zoledronic acid, and at least another bioactive agent, such as fosfomycin or a pharmaceutically acceptable salt thereof.

In fact, fosfomycin accelerates curing of a composition comprising hydroxyapatite and may improve mechanical stability of said composition in-situ.

The bone reconstruction composition may also comprise a cytostatic agent. Cytostatic agents, such as Bendamustine, Busulfan, Carmustine, Chlorambucil, Cyclophosphamide, Dacarbazine, Ifosfamide, Melphalan, Procarbazine, Streptozocin and Temozolomide or derivatives thereof may thus also be comprised in the bone reconstruction composition. The bone reconstruction composition can in a similar way comprise an antiviral compound, an antifungal compound, a tuberculostatic or tuberculocidal compound or an antiparasite compound or a genetically altered variant of the aforementioned for the purpose of targeted antitumor treatment.

Another additive, which may be included in the bone reconstruction composition, is a non-ionic X-ray contrast agent.

The antibiotic agent may be present within the composition in any suitable amount. For example, at least 80 mg/ml, such as at least 97 mg/ml, such as at least 110 mg/ml, and up to 200 mg/ml, such as up to 175 mg/ml of said antibiotic or antibiotic mixture, where ml refers to the final volume of the composition.

Different types of antimicrobial/anti-biofilm agents may be comprised in the bone reconstruction composition to complement each other and deliver synergistic antimicrobial effects to the site of the bone defect. Said bioactive agents will spread into the biocompatible matrix e.g. the bone graft material as well as into the area around the bone defect, e.g. into local hematoma and/or seroma by way of elution and diffusion from the composite.

A list of anti-microbial agents suitable for use in combination with biocompatible materials, such as for preventing or treating colonization of said materials by microorganisms can be found in Campoccia et al. (2013. A review of the biomaterials technologies for infection-resistant surfaces Biomaterials, 34(34): 8533-8554).

In one embodiment of the present disclosure, the at least one bioactive agent comprises or consists of a biofilm preventing, dispersing or disrupting agent, also referred to as anti-biofilm agent. Several compounds act as anti-biofilm agent, for example non-antibiotic compounds with innate antibacterial properties, such as silver and copper; N-acetylcysteine; nitric oxide (NO)-releasing coatings with diazeniumdiolates or calcium peroxide; bioactive antibacterial coatings; antimicrobials able to bypass the biofilm barrier, such as Daptomycin or, Minocycline; peptides such as human β-defensin-3; cyclic di-GMP modulating proteins; the transcriptional regulatory protein MucR; nanostructured compounds such as silver or chitosan; enzymes that lyse certain elements of the biofilm e.g. dispersin B or proteinase K. Also cytotoxic agents, which are described in detailed above, have been found to be successful in removing biofilms from implant surfaces. For example, citric acid was found to be successful in eliminating biofilms from titanium surfaces. A list of other agents that inhibit biofilm formation is found in Rabin N et al. (Rabin N, Zheng Y, Opoku- Temeng C, Du Y, Bonsu E and Sintim HO, Future Medicinal Chemistry, 2015, 7(5):647-671).

Growth Promoting Agents

The bone reconstruction compositions described by the present invention may comprise agents that stimulate and/or accelerate bone formation (also referred to as "growth promoting agents"), such as osteoinductive agents, growth factors and hormones. Specific signaling molecules, growth factors and derivatives thereof, which are locally acting are preferred. Said agents may be released from the composition in vivo.

Appropriate stem cell differentiation and subsequent bone formation requires concerted generation, conduction and regulation of a range of specific signaling molecules, including various enzymes, growth factors and hormones. The biocompatible carrier of the present disclosure is also an effective delivery vehicle for bioactive agents such as growth factors and antiresorptive agents.

It is preferred to use autologous signaling molecules and growth factors, which are effective in connection with bone, tendon or cartilage. Thus, the bone reconstruction composition may comprise at least one growth or differentiation factor selected from the group consisting of bone morphogenic proteins (BMPs), members of the TGF-superfamily, platelet-derived growth factor (PDGF), fibroblast growth factors (FGFs), insulin-like growth factors (IGFs), metalloproteinases, vascular endothelial growth factor (VEGFs A, B, C or D), angioprotein 1 and 2, and combinations thereof. These endogenously produced growth factors are used as an additive either as single entities or combined in a growth factor mixture in order to accelerate bone growth. Thus, it is preferred that an endogenously produced bioactive molecule is used as a substance that induces bone formation.

In one embodiment of the disclosure the growth promoting or osteoinductive agent is a bone morphogenic protein (BMP, for example the growth promoting agent may be selected from the group consisting of BMP1, BMP2, BMP3, BMP4, BMP5, BMP6, BMP7, BMP8a, BMP8b, BMP10, BMP15 and a combination thereof. Preferably, said BMPs are BMPs of the same species to be treated with the bone reconstruction composition. Thus, the BMP may be human BMP, for example the growth promoting agent may be selected from the group consisting of human BMP1, human BMP2, human BMP3, human BMP4, human BMP5, human BMP6, human BMP7, human BMP8a, human BMP8b, human BMP10, human BMP15 and a combination thereof. The term "human BMP" as used herein refers to wild type human BMP.

Examples of other growth promoting agents are parathyroid hormones and derivatives thereof, estrogens, progesterone, androgens, testosterones, calcitonin, somatomedin, and oxytocin, preferably also autologous, but they can also be produced according to procedures known within the art.

Other Bioactive Agents

The bone reconstruction compositions described by the present disclosure comprise at least one bioactive agent e.g. a biologically and/or therapeutically active agent, also referred to as bioactive agent. In addition to bisphosphonates, anti-microbial agents and growth promoting agents, other bioactive agents may be comprised in the composition, as described here below.

In one embodiment of the present disclosure, the at least one bioactive agent comprises or consists of a BMP antagonist inhibitors selected from the group consisting of noggin, chordin, sclerostin, follostatin.

In one embodiment of the present disclosure, the at least one bioactive agent comprises or consists of a BMP antagonist inhibitors selected from the group consisting of members of the DAN family, for example sclerostin, members of the twisted gastrulation family and noggin/chordin.

In one embodiment of the present disclosure, the at least one bioactive agent comprises or consists of a signaling protein, for example a signaling protein selected from the group consisting of Wnt proteins, lymphoid enhancer-binding factor 1 (Lef1), β-catenin, parathyroid hormone-related protein (PTHrP), colony stimulating factors, Indian hedgehog homolog (IHH), Hypoxia-inducible factor 1-alpha (HIF-α) and combinations thereof.

Healing and generation of new mineralized tissue in bone defects, the so-called osteogenesis involves active participation of various types of cells, including osteoblasts, chondroblasts, osteocytes and osteoclasts. Bone formation is the result of successful recruitment and differentiation of locally available and/or implanted pluripotent progenitor cells into mature bone matrix producing cells at the site of the lesion. Suspensions of pluripotent mesenchymal stem cells (MSC's) and/or platelet rich plasma (PRP) can be harvested form a variety of sources (e.g. blood, bone marrow and/or adipose tissue), incorporated into an appropriate biocompatible carrier, preferably comprising an osteoconductive material, and thus delivered to the site of a bone defect as part of the method disclosed herein.

Similarly, other types of cells, such as for example tumor infiltrating lymphocytes could be incorporated in a similar fashion into a surgically treated bone tumor site, to allow local delivery of cells for specific purposes, such as the killing of tumor cells, which may enhance local recurrence rates.

Therefore, in one embodiment of the present disclosure, the at least one bioactive agent comprises or consists of a human cell suspension, for example a human cell suspension comprising or consisting of mesenchymal stem cells and/or lymphocytes and/or platelet depleted plasma and/or lipoaspirate of autogenic or allogenic origin such as the stromal vascular fraction.

In some embodiments of the present disclosure, cell suspensions are added to or substitute part of the solvent comprised in the biocompatible carrier.

In cases of treatment of metastatic bone lesions or pathologic fractures, placement of pellets or seeds in the biocompatible carrier would permit localized internal radiation therapy of eventual residual tumor tissue. The internal radiation therapy delivered from radiation sources placed inside or on the body is termed brachytherapy. In brachytherapy, radioactive isotopes are sealed in tiny pellets or "seeds" which can be delivered to patients using delivery devices, e.g. an appropriate biocompatible carrier, such as a carrier comprising an osteoconductive material. As the isotopes decay naturally, they give off radiation that damage nearby cancer cells. If left in place, after a few weeks or months, depending on the isotope, the isotopes decay completely and no longer give off radiation. The seeds will not cause harm if they are left in the body. Brachytherapy may be able to deliver higher doses of radiation to some sites than external-beam radiation therapy while causing less damage to normal tissue.

The seeds can be resorbable or non-resorbable.

The placement of brachytherapy sources can be temporary or permanent. These particles or seeds may be also embedded into the biocompatible matrix.

In some embodiments, these solid particles are embedded into the biocompatible carrier.

Therefore, in one embodiment of the present disclosure, the at least one bioactive agent comprises or consists of a radioactive material, for example a radioactive material selected from the group consisting of Cesium-131 or Cesium-137 or Cobalt-60 or Iridium-192 or Iodine-125 or Palladium-103 or Ruthenium-106 or Radium-226 and combinations thereof.

In one embodiment of the present disclosure, the at least one bioactive agent comprises or consists of a cytokine, for example a cytokine selected from the group consisting of interleukin-1 (IL-1) or interleukin-6 (IL-6) or tumor necrosis factor alpha (TNF-alpha) or receptor activator of nuclear factor kappa-B ligand (RANKL) or core-binding factor alpha 1 (cbfa1) or osteogenin or SMADs proteins 1-8 or osteogenic growth peptide (OGP) and combinations thereof.

In one embodiment of the present disclosure, the biocompatible carrier comprises a solvent, for example a solvent selected from the group consisting of water, simple sugars such as for example glucose, fructose, mannitol, a contrast agent such as iohexol, platelet depleted plasma, lipoaspirate, fosfomycin, vancomycin or gentamycin and combinations thereof.

In one embodiment of the present disclosure, the at least one bioactive agent comprises or consists of an antiadhesive agent, for example monomeric trimethylsilane (TMS) or nonionic surfactants, e.g Pluronic F127.

In one embodiment of the present disclosure, the at least one bioactive agent may be an antimetabolite, a chemical that inhibits the use of a metabolite which is part of the normal metabolidm of the subject. The antimetabolite is selected from the group consisting of Asparaginase, Capecitabine, Cytarabine, 5-Fluoro Uracil, Fludarabine, Gemcitabine, Methotrexate, Pemetrexed and Raltitrexed.

In another embodiment of the present disclosure, the at least one bioactive agent may be an anti-tumour antibiotic selected from a group composed of Actinomycin D/Dactinomycin, Bleomycin, Daunorubicin, Doxorubicin, Doxorubicin (pegylated liposomal), Epirubici, Idarubicin, Mitomycin and Mitoxantrone.

In another embodiment of the present invention, bioactive agents, e.g. biologically and/or therapeutically active agents, may be plant alkaloids/microtubule inhibitors selected from a group composed of Etoposide, Docetaxel, Irinotecan, Paclitaxel, Topotecan, Vinblastine, Vincristine and Vinorelbine.

In another embodiment of the present disclosure, the at least one bioactive agent may be a DNA linking agent including Carboplatin, Cisplatin and Oxaliplatin.

In another embodiment of the present disclosure, the at least one bioactive agent may be a hormons including Anastrozole, Abiraterone, Amifostine, Bexarotene, Bicalutamide, Buserelin, Cyproterone, Degarelix, Exemestane, Flutamide, Folinic acid, Fulvestrant, Goserelin, Lanreotide, Lenalidomide, Letrozole, Leuprorelin, Medroxyprogesterone, Megestrol, Mesna, Octreotide, Stilboestrol and Tamoxifen.

Biocompatible Matrix

The kit-of-parts and the methods for treatment of a bone defect described in the present invention comprise a biocompatible matrix e.g. a bone graft material comprising solid particles of natural or synthetic origin. Also compositions of the invention may comprise a biocompatible matrix.

In a preferred embodiment, said particles comprise or consist of synthetic metallic structural scaffolds and/or particles or synthetic non-metallic scaffolds and/or particles or cancellous bone or combinations thereof.

In another preferred embodiment said particles comprise of consist of a bone graft material, e.g. a bone graft material as described below.

The presence of solid particles and/or scaffolds in the biocompatible matrix adds mechanical stability to the bone reconstruction composition and diminishes the risk of premature loss of mechanical stability, liquefaction and/or resorption of the bone reconstruction composition.

In some embodiments of the present disclosure, the particles of the biocompatible matrix comprise or consist of synthetic non-metallic scaffolds and/or particles and wherein said scaffold and/or particles are 3D-printed.

In some embodiments, the particles of the biocompatible matrix comprise or consist of synthetic metallic scaffolds and/or particles, such as spheres or scaffolds. The synthetic metallic particles may comprise or consist of titanium or tantalum.

The particles of the biocompatible matrix preferably have a particle size of at least 0.5 mm, such as at least 1 mm, such as at least 2 mm, such as at least 3 mm. Said particles may have any shape, they can for example be diamonds, spheres or cubes.

Other examples of synthetic metallic structural scaffolds and/or particles or synthetic non-metallic scaffolds and/or particles are natural or synthetic polymers, composites (chitosan, collagen etc. ceramics, PEEK, carbon fiber reinforced PEEK, carbon) and natural coralline hydroxyapatite.

Bone Graft Material

In some embodiments of the present disclosure, the biocompatible matrix comprises or consists of a bone graft material. Thus, the methods may comprise impacting a damaged bone with the bone reconstruction composition and biocompatible matrix components such as said bone graft material and/or synthetic particles.

The bone graft material comprises bone from a human or non-human animal. It is preferred that the bone graft material comprises bone from the same species, as the species to be treated with the bone graft material. Thus, frequently it is preferred that said bone graft material comprises bone from a human being.

In preferred embodiments of the invention, the bone graft material consists of bone from a human or non-human animal. In particular, the bone graft material may consist of human bone.

Said bone graft material may be autogenic or allogenic bone, i.e. the bone graft material may comprise or consist of bone from the individual to be treated, or it may comprise or consist of bone from another individual of the same species, or a combination of both.

Therefore, in some embodiments of the present disclosure, the biocompatible matrix, e.g. a bone graft material, comprises particles of cancellous bone, wherein the cancellous bone is allograft and/or autograft.

For example the biocompatible matrix e.g. the bone graft material may essentially consist of cancellous bone, i.e. at least 70%, preferably 80%, such as at least 85% of the biocompatible matrix consists of cancellous bone, for example human cancellous bone. The remainder of the biocompatible matrix may consist of remnants of material naturally associated with cancellous bone, for example cortical bone, soft tissues of bone, lipids and/or blood. In some embodiments, the cancellous bone comprises no more than 10% water and no more than 5% lipids.

In some embodiments of the present disclosure, said bone graft material comprises demineralized bone matrix.

In some embodiments of the present disclosure, said bone graft material comprises between 1 and 10 ml of demineralized bone matrix.

In some embodiments of the present disclosure, said bone graft material comprises between 1 and 10 g of demineralized bone matrix.

In some embodiments of the present disclosure, said bone graft material is allograft and/or autograft bone, for example vascularized autograft.

Frequently, said bone, e.g. cancellous bone is present in the biocompatible matrix e.g. in the bone graft material in the form of smaller particles, for example in particles having a particle size of no more than 5 mm, such as no more than 4 mm, for example no more than 3 mm, for example in the range of 2 to 3 mm. In particular, the bone, e.g. cancellous bone may be present in the bone graft material in the form of smaller particles having a size in the range of −3.5 to −6 mesh, for example in the range of −4 to −6 mesh, such as in the range of −5 to −6 mesh. A "-" before the sieve mesh indicates the particles pass through the sieve. Thus, by way of example if a material is described as −6 mesh, then 90% or more of the material will pass through a 6-mesh sieve.

Said bone, e.g. cancellous bone may undergo processing that may comprise fragmenting the material, cleaning the material and/or disinfecting the material before it is ready for use as a biocompatible matrix. Said bone in the form of particles may be prepared by milling, crushing or other mean of fragmentation. For example, the bone in the form of particles may be prepared using a bone mill or a device having the same function.

In a preferred embodiment, said biocompatible matrix e.g. bone graft material is frozen cancellous allograft bone taken from a hospital bone bank and stored as per the routine procedure of the hospital. Such material may be devoid of cortical and soft tissue remnants.

In another embodiment, said biocompatible matrix e.g. bone graft material is autograft bone, wherein said bone is cancellous autograft or corticocancellous autograft shaped and applied into the outer surface areas of an individual bone defect in the area of a cortical window. In this embodiment, longer curing time and more compression during curing may apply due to the higher content of blood and other liquids typically present in autograft material.

In an embodiment of the present invention, said biocompatible matrix e.g. bone graft material comprises cells capable of true osteogenesis. For example when cancellous autograft and/or autograft harvested using the Reamer-Irrigator-Aspirator technique (RIA autograft) is used.

Curing of Composition

In a preferred embodiment of the present invention, said composition used is cured to allow setting. Although said curing can occur spontaneously, improved interdigitation with host bone and biocompatible matrix, e.g. bone graft material, may be achieved by keeping the material under compression with a gauze material after sequential impaction until setting is complete. The curing procedure may be performed for few minutes and/or until complete setting.

In a preferred embodiment of the present disclosure, the bone reconstruction composition cures in a time range of 2 to 60 minutes after all ingredients of said composition are mixed. The curing time may vary, it can for example be 2 to 50 minutes, preferably 2 to 40 minutes, preferably 2 to 30 minutes, preferably 2 to 20 minutes, preferably 2 to 10 minutes, preferably 2 to 5 minutes, preferably 2 to 3 minutes.

In a preferred embodiment of the present disclosure, the bone reconstruction composition thickens to a paste in a time range of 2 to 10 minutes after all ingredients of said composition are mixed, such as in a time range of 2 to 8 minutes, such as in a time range of 2 to 7 minutes, such as in a time range of 2 to 6 minutes, such as in a time range of 2 to 5 minutes, such as in a time range of 2 to 3 minutes after all ingredients of said composition are mixed.

Method of Producing Bone Reconstruction Composition

In an embodiment of the present invention, a composition to be used together with bone graft material for treatment of bone defect is prepared. The bone reconstruction composition may be prepared by any useful method.

In one embodiment the bone reconstruction composition may be prepared by a method comprising the steps of:
  a. providing a biocompatible carrier
  b. providing one or more bioactive agents, e.g. an antiresorptive agent, an antibiotics, or other agents described in the section "Bioactive agent"
  c. optionally providing a solvent
  d. mixing said the biocompatible carrier with the one or more bioactive agents and optionally with a solvent until a paste is formed
  e. optionally adding additional bioactive agents in solvent followed by mixing.

In some embodiments, the bioactive agents are provided in a solvent.

In other embodiments, additional solvent is added to the mixture, said solvent being free from bioactive agents or comprising one or more bioactive agents.

In one embodiment the bone reconstruction composition may be prepared by a method comprising the steps of:
  a. providing hydroxyapatite (HA) and calcium salt
  b. mixing hydroxyapatite and calcium salt
  c. providing an antiresorptive agent, e.g. a bisphosphonate contained in a solvent
  d. mixing said antiresorptive agent in said solvent with HA and calcium salt until a paste is formed
  e. optionally adding additional antiresorptive agent in solvent followed by mixing.

Mixing of steps d. and e. may be for any suitable time, for example for in the range of 1 to 10 min. such as in the range of 2 to 3 min. The solvent may be any useful solvent e.g. water. Said water may comprise additives, such as a buffer, a salt and/or other components e.g. mannitol. Thus, the solvent may be a buffered saline aqueous solution, e.g. a citrate buffered aqueous solution comprising a physiological level of salt, e.g. in the range of 0-7 to 1.0%, such as approximately 0.9% NaCl.

One specific example of a useful method to prepare composition comprises the following steps:
  f. providing hydroxyapatite (HA) and calcium sulfate
  g. putting hydroxyapatite and calcium sulfate in a ration 40:60 into a device that allows mixing
  h. drawing up zolendric acid
  i. adding an appropriate amount of zolendric acid into the device for mixing, already containing HA and calcium sulfate
  j. mixing till a paste is formed, having toothpaste consistency
  k. after 3 minutes from the moment mixing was started, the mixing is stopped for 10-20 seconds to allow stiffening
  l. more zolendric acid is added and the mixing repeated
  m. after 3 further minutes the composition reaches the desired consistency
  n. the composition is delivered into the bone cavity within the next 3 minutes.

The composition may comprise at least 50% of HA and calcium sulfate. The composition may also comprise at least 0.3 mg/ml of ZA, preferably approximately 0.55 mg/ml and up to 0.80 mg/ml, where ml refers to the final volume of the composition.

In a preferred embodiment of the invention, a longer setting time is allowed, so that the composition reaches a harder consistency. The resulting mould is applied directly without the help of a syringe.

In some embodiments of the present disclosure, one or more bioactive agents are added to the composition. Some bioactive agents are in liquid forms and are added to the composition as they are. Some bioactive agents are not in liquid form and thus they are first mixed with a solvent and dissolved, and only after they are added to the mixture.

In the sections above "Bioactive agents", "Bisphosphonate", Antimicrobial agents", "Growth promoting agents" and "Other bioactive agents" there are details regarding the various types of agents can be beneficially be added to the composition.

In another embodiment of the present invention, an antibiotic is added to said composition. The antibiotic may be mixed with a suitable solvent prior to its addition to the composition. The dissolved antibiotic may be added into the mixing device containing BGS prior to addition of zolendric acid. The dissolved antibiotic may be added into the mixing device containing BGS after addition of zolendric acid. The composition may comprise at least 80 mg/ml, such as at least 97 mg/ml, such as at least 110 mg/ml, and up to 175 mg/ml of said antibiotic or antibiotic mixture, where ml refers to the final volume of the composition.

Another example of a useful method to prepare composition comprises the following steps:
 a. providing hydroxyapatite (HA) and calcium sulfate
 b. putting hydroxyapatite and calcium sulfate in a ration 40:60 into a device that allows mixing
 c. drawing up 1 mg zolendric acid 1 g fosfomycin in 10 ml solvent
 d. adding said solvent, containing zoledronic acid and fosfomycin into the device for mixing, already containing HA and calcium sulfate
 e. mixing till a paste is formed, having toothpaste consistency
 f. allowing the paste to set for 1-3 minutes until the composition reaches the desired consistency
 g. delivering the composition into the bone cavity within the next 3 minutes.

In a preferred embodiment, the antibiotic added is fosfomycin. In another embodiment the antibiotic gentamicin or vancomycin is added. Additional anti-microbial agents may be added as described in the section "Antibiotic".

Method for Bone Reconstruction

The present invention describes methods for treatment of a bone defect in a subject, said treatment comprising providing a biocompatible carrier, providing biocompatible matrix, e.g. a bone graft material, and providing impacting a bone defect with said biocompatible carrier and said biocompatible matrix in alternate layers to achieve a mechanically stable bone reconstruction construct, as described in the detail in the section above "Treatment of bone defects".

As the bone reconstruction composition typically contains the bioactive agents, it is applied over the entire surface of all relevant areas of the individual defect and in direct contact with the local host bone. Then, the biocompatible matrix is impacted in the bone defect applying a certain pressure. This layer is covered by impacting said composition comprising one or more bioactive agents over it. This second layer may also be covered with further biocompatible matrix. This third layer may be further covered with said composition comprising one or more bioactive agents. The procedure is repeated until the desired level of defect fill is achieved. Impacting the reconstruction construct within said bone defect with said composition and said biocompatible matrix during or at the end of the reconstruction process can contribute to achieve a denser and more mechanically stable bone reconstruction construct.

Bone defect reconstruction may require additional mechanical stabilization with appropriate internal or external bone fixation devices including but not limited to standard or custom wires, pins, screws, plates, nails, prosthetic-and/or external fixation devices, but also auto- or allograft bone with- or without vascularized bone grafts, which can help reinforcing the structure of the defected bone.

In one embodiment of the invention, said method comprises forming at least 2 layers, one comprising the biocompatible matrix and one comprising the bone reconstruction composition, so that the bone defect is repaired.

In a preferred embodiment, said method comprises forming at least 3 layers, such as at least 4 layers, such as at least 5 layers, such as at least 6 layers, wherein at least one comprises the biocompatible matrix and at least one comprises the composition, so that the bone defect is repaired.

In one aspect, the present disclosure relates to a method for bone reconstruction in an individual suffering from a bone defect, said method comprising performing the method as described herein, thereby obtaining growth of healthy bone on the site of the bone defect in said individual.

EXAMPLES

Example 1. Reconstruction of Metastatic Bone Defects with a Bisphosphonate Eluting Bone Graft Substitute Six patients (5f, 1 m, mean age 64 (range 37-81) who had undergone reconstruction of metastatic bone defects with implantation of a gentamycin eluting sulfate-apatite bone graft substitute (Cerament™1G, BONESUPPORT, Lund, Sweden) which was additionally loaded with zoledronic acid, were prospectively followed for a mean of 12 months (range 6-17). In all 5 female patients, the indication for treatment was a partially contained bone defect associated with incipient or actual pathologic fracture of the acetabulum (n=3) or proximal humerus (n=2) secondary to metastatic breast cancer. The only male patient had wide resection of a solitary lung cancer metastasis from the proximal femur.

Sequential imaging (X-ray/CT) demonstrated progressive consolidation of the inserted graft material without any evidence of persistent osteolysis or local recurrence. Rapid and homogeneous remodeling typically started in well-contained areas with cancellous bone contact. Substantial bone formation was also observed in uncontained areas where graft material had been applied to the surface of metallic implants or surrounding cortical bone in some cases.

Example 2. Early Clinical Experience with Local Bisphosphonate Delivery for Bone Defect Reconstruction in Aggressive Benign Bone Tumors 11 patients (9f, 2m, mean age 35 (range 18-62)) with aggressively behaving benign bone tumors (5 GCT, 4 ABC, 2 UBC) who underwent tumor resection with curettage, high speed burring and subsequent bone defect reconstruction utilizing a combination of a biocompatible carrier, e.g. gentamycin eluting bone graft substitute (Cerament™1G, BONESUPPORT, Lund, Sweden) and a biocompatible matrix, e.g. cancellous allograft, with serial imaging (X-ray/CT) were prospectively followed for a mean of 12 months (range 6-24).

Figure 6:
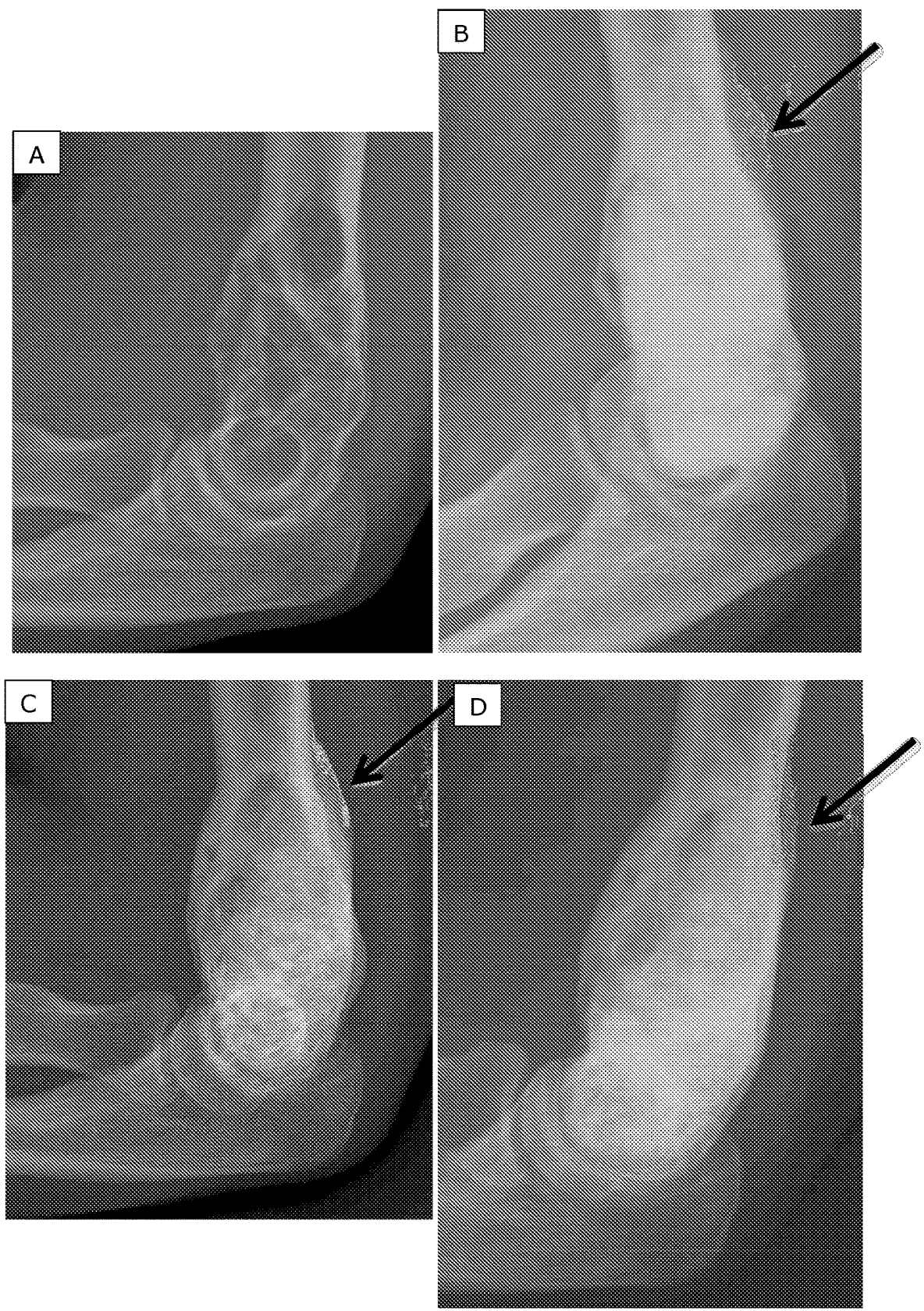
FIG. 6. 38 year old female with symptomatic vascular malformation with secondary aneurysmal bone in the left distal humerus, treated with open biopsy, curettage, burring, bone defect reconstruction with a combination of BGS/ZA and cancellous allograft. Post-op x-rays and CT scans show homogenous, progressive remodeling of the entire regenerate as well as substantial periosteal bone formation (arrows). a. pre-operative; b. post-operative; c. 3 months and d. 6 months.

Radiographic evidence of local bone formation and remodeling by far exceeded rates and amounts usually observed with either single component alone. Rapid and homogeneous remodeling typically started in areas with cancellous bone contact in the periphery of the defects but was not limited to the cavities only. Substantial periosteal bone formation was also observed in areas of ungrafted surrounding cortical bone. In the FIGS. 1-6 and 10, x-rays taken prior treatment, right after and few months after treatment show bone formation and remodeling in 6 different patients. In particular, the treatment represented in FIGS. 1-6 and 10 was performed by applying a biocompatible matrix, e.g. cancellous allograft, and a bone reconstruction composition, e.g. bone graft substitute (BGS) comprising zoledronic acid and they all show new bone formation and remodeling at 3 weeks to 6 months after treatment. FIG. 6 shows also achievement of periosteal callus formation.

Figure 7:
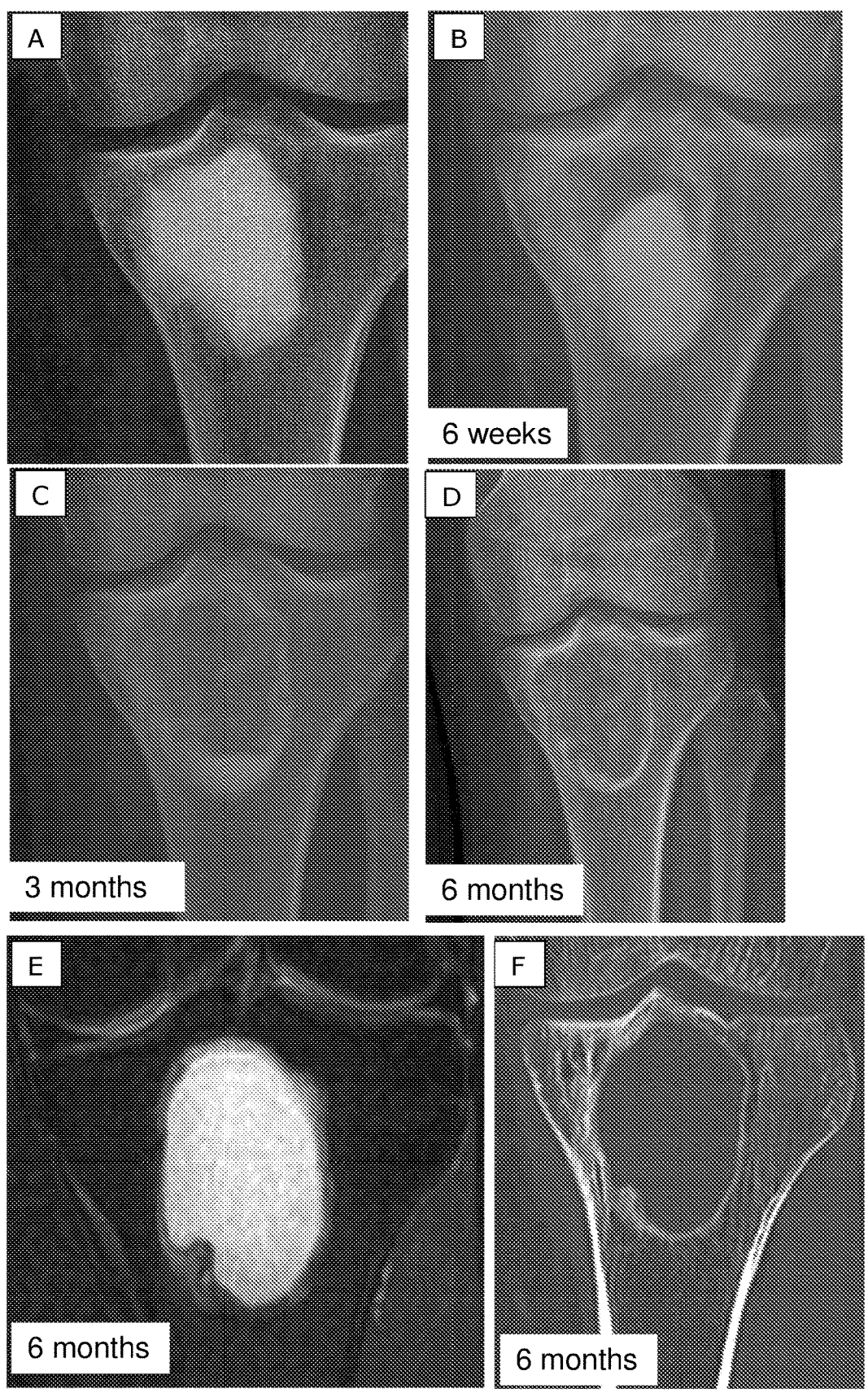
FIG. 7. 35 year old female with benign bone lesion (probably old bone infarct) in the proximal tibia, treated with open biopsy, curettage, burring, bone defect reconstruction with Cerament BVF (17 ml) only (A). Post op radiographs show progressive resorption (B) and liquefaction (C) and ultimately complete disappearance of the BGS without any sign of bone formation on x-ray, MRI or CT scanning (D,E,F). a. post-operative; b, 6 weeks, c. 3 months and d, e and f. 6 months.
Figure 8:
FIG. 8. 68 year old male with aseptic loosening of an intercalary diaphyseal replacement in the right femur (A), treated with 2 stage revision and intermediate implantation of an antibiotic cement spacer (B) and re-implantation of a new, cemented, silver coated intercalary spacer and periprosthetic bone defect reconstruction (C). A composite of RIA-autograft from the contralateral femur, Cerament G with ZA, DBM and allograft were applied postero-medially, while the remaining defect anterolaterally (arrow) was filled with BGS only. Radiographic follow up at 6 months shows substantial new bone formation in the area where the bioactive composite had been applied, whereas the area treated with the BGS only shows resorption of all material applied to this area and no evidence of bone formation (D). a. pre-operative, b. post-operative (1st stage), c. post-operative (2nd stage), d. 6 months.
Figure 8:
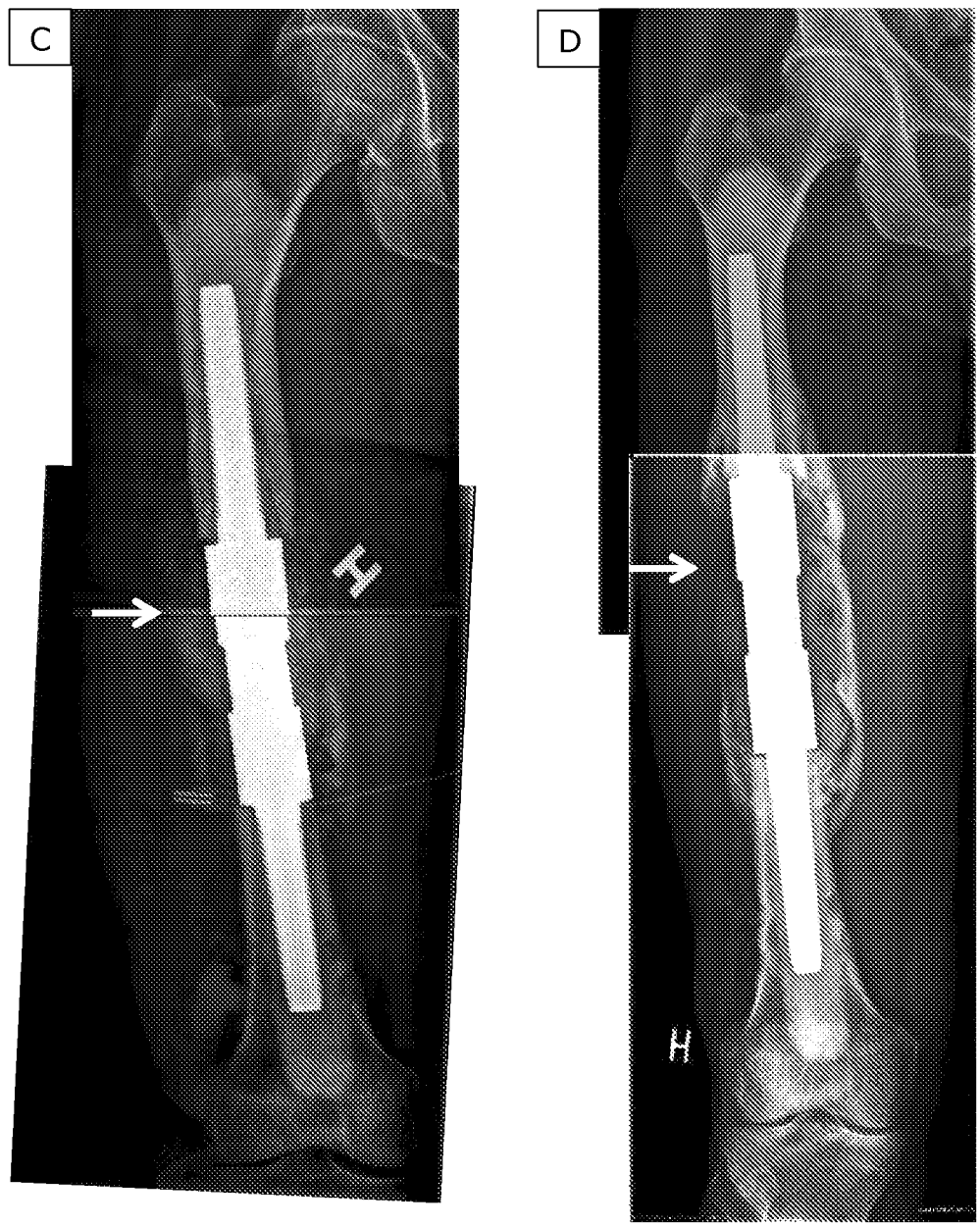
Figure 9:
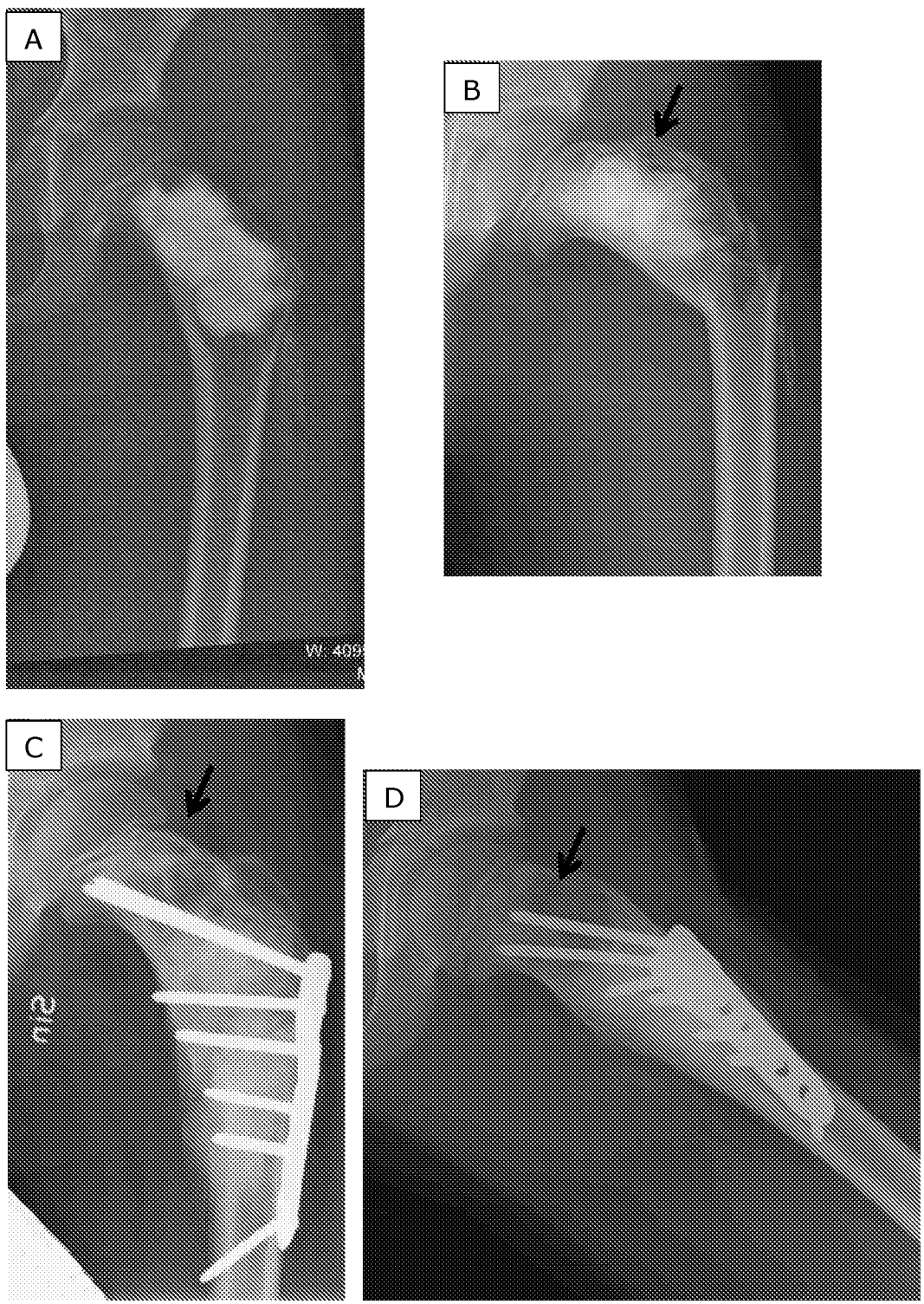
FIG. 9. 8 year old boy with a large simple cyst in the left proximal femur, treated with percutaneous injection of Cerament BVF (A). Immediate post-operative radiographs show almost complete filling of the cyst. 3 weeks post-operatively, the boy suffers a spontaneous fracture of the proximal femur though one of the BGS injection portals (B). A revision operation is carried out, where parts of the BGS in the area of the fracture are removed, but the cranial two thirds appear structurally intact and are left in place (B, arrow). After reconstruction of the remaining defect in the region of the fracture with Allograft, BGS+ZA and DBM, a pediatric LCP is applied to internally fix the fracture. Post-operative follow-up radiographs show sound progressive consolidation and remodeling of the fracture, while the BGS in the cranial parts of the cyst is progressively resorbed without any evidence bone formation in the femoral neck (arrows, C and D).
Figure 10:
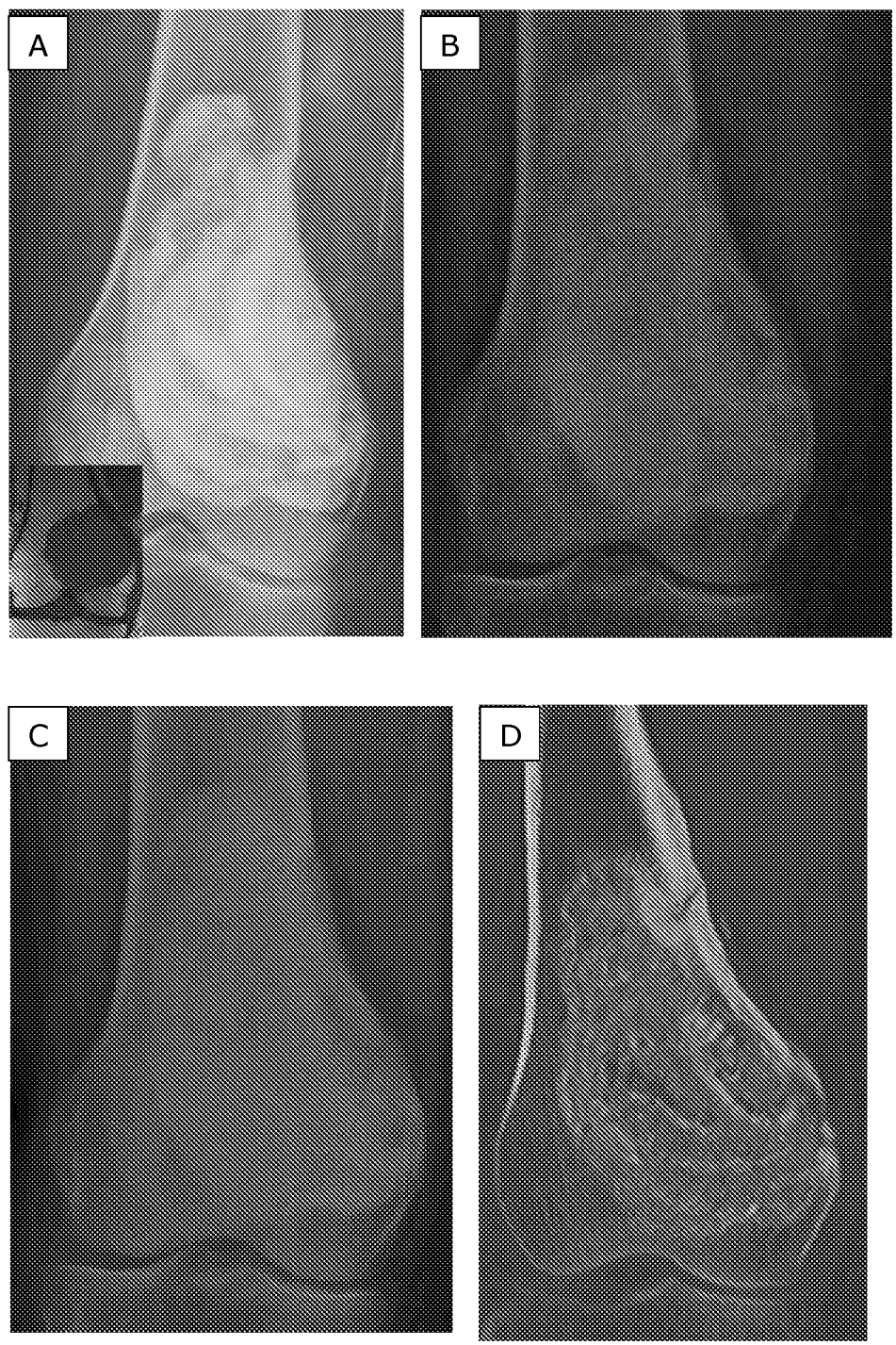
FIG. 10. 67 year old female with symptomatic giant cell tumor of bone in the medial femoral condyle, treated with open biopsy, curettage, burring, bone defect reconstruction with a combination of BGS/ZA and cancellous allograft. Overall stability of the bone was deemed sufficient so that plate augmentation was not necessary. Immediate post a-p radiographs show complete tumor removal and defect filling in several ALIG layers (A). Follow up x-rays and CT scans show progressive homogenous remodeling of the entire regenerate. a. pre-operative (inset), post-operative, b. 6 months, c and d. 12 months.

The treatment represented in FIG. 7, instead, was performed by applying only a bone reconstruction composition, e.g. the bone graft substitute (Cerament™|BVFG, BONESUPPORT, Lund, Sweden) not comprising zoledronic acid or any other bioactive agent. As shown in FIG. 7, complete disappearance of the bone graft substitute is observed 6 months after the treatment. The patient represented in FIG. 8 was affected by aseptic loosening of an intercalary diaphyseal replacement in the right femur, treated with 2 stage revision and intermediate implantation of an antibiotic cement spacer and re-implantation of a new, cemented, silver coated intercalary spacer and periprosthetic bone defect reconstruction. Part of the bone defect was filled using a biocompatible matrix, e.g. RIA autograft, DBM and allograft, and a biocompatible carrier comprising Cerament G with zoledronate (ZA) in layers, which resulted in substantial new bone formation at 6 months (FIG. 8D). The remaining part of the bone defect was treated with only bone graft substitute (BGS) which showed no evidence of bone formation at 6 months (FIG. 8D, arrow). The patient represented in FIG. 9 was affected by a large simple cyst in the left proximal femur, which was in a first instance treated by percutaneous injection of a biocompatible carrier alone, e.g. the bone graft substitute Cerament BVF, not comprising bioactive agents. 3 weeks post-operatively, the patient suffers a spontaneous fracture of the proximal femur though one of the BGS injection portals (FIG. 9B). So part of the bone graft substitute was removed and replaced with a biocompatible matrix, e.g. allograft, and bone graft substitute supplemented with zoledronate and demineralized bone matrix (FIG. 9B), whereas the cranial two thirds appeared structurally intact and were left in place (FIG. 9B, arrow). Post-operative follow-up radiographs show sound progressive consolidation and remodeling of the fracture (FIGS. 9C and D), while the non-substituted part progressively resorbed without any evidence bone formation in the femoral neck (FIGS. 9C and D, arrows).

These examples are only exemplary and do not disclose the true scope of the invention.

The invention claimed is:

1. A method for treatment of a bone defect in an individual in need thereof, which method comprises:
   providing a bone reconstruction composition comprising a biocompatible carrier and at least one bioactive agent,
   providing a biocompatible matrix comprising solid particles and/or scaffolds of natural or synthetic origin,
   contacting the site of a bone defect in said individual with alternating layers of said composition and said biocompatible matrix thereby treating said bone defect.

2. The method according to claim 1, wherein the biocompatible carrier comprises calcium salts, hydroxyapatite and natural and/or synthetic polymers.

3. The method according to claim 1, wherein the biocompatible carrier comprises calcium sulfate and/or calcium phosphate.

4. The method according to claim 1, wherein the at least one bioactive agent comprises or consists of a growth or differentiation factor.

5. The method according to claim 1, wherein the at least one bioactive agent comprises a human cell suspension.

6. The method according to claim 1, wherein the biocompatible carrier comprises a solvent.

7. The method according to claim 1, wherein the at least one bioactive agent further comprises fosfomycin or a pharmaceutically acceptable salt thereof.

8. The method according to claim 1, wherein the bone reconstruction composition comprises two or more bioactive agents.

9. The method according to claim 1, wherein the bone reconstruction composition comprises two or more bioactive agents, wherein at least one of the bioactive agents accelerates curing of the composition and wherein at least one of the bioactive agents decelerates curing of the composition.

10. The method according to claim 9, wherein the bioactive agent that accelerates curing of the composition is an antibiotic.

11. The method according to claim 9, wherein the bioactive agent that decelerates curing of the composition is a bisphosphonate.

12. The method according to claim 1, wherein the particles and/or scaffolds of the biocompatible matrix comprises or consists of synthetic metallic structural scaffolds and/or particles or synthetic non-metallic scaffolds and/or particles or cancellous bone or combinations thereof.

13. The method according to claim 1, wherein the particles and/or scaffolds of the biocompatible matrix comprises or consists of bone graft material.

14. The method according to claim 1, wherein the biocompatible matrix comprises particles of cancellous bone and wherein the cancellous bone is allograft and/or autograft.

15. The method according to claim 1, wherein the biocompatible matrix comprises particles of cancellous bone and wherein said cancellous bone comprises demineralized bone matrix.

16. The method according to claim 1, wherein the biocompatible matrix comprises particles of cancellous bone, wherein the cancellous bone is autograft and wherein said autograft is vascularized.

17. The method according to claim 1, wherein said bone reconstruction composition and said biocompatible matrix are impacted in at least 2 alternate layers, or at least 4 alternate layers, or at least 6 alternate layers, wherein at least one layer comprises or consists of said bone reconstruction composition and at least one layer comprises or consists of said biocompatible matrix.

* * * * *